(12) United States Patent
Sugimura et al.

(10) Patent No.: US 7,491,803 B2
(45) Date of Patent: Feb. 17, 2009

(54) HUMAN ANTI-HUMAN INTERLEUKIN-18 ANTIBODY, FRAGMENT THEREOF AND METHOD FOR USING SAME

(75) Inventors: Kazuhisa Sugimura, Kagoshima (JP); Kenji Nakanishi, Nara (JP); Toshihiro Nakashima, Kumamoto (JP)

(73) Assignees: Japan Science & Technology Agency, Kawaguchi (JP); Juridical Foundation The Chemo-Sero-Therapeutic Research Institute, Kumamoto-Shi (JP)

( * ) Notice: Subject to any disclaimer, the term of this patent is extended or adjusted under 35 U.S.C. 154(b) by 88 days.

(21) Appl. No.: 10/555,074

(22) PCT Filed: Apr. 30, 2004

(86) PCT No.: PCT/JP2004/006403

§ 371 (c)(1),
(2), (4) Date: Oct. 28, 2005

(87) PCT Pub. No.: WO2004/097019

PCT Pub. Date: Nov. 11, 2004

(65) Prior Publication Data

US 2006/0292145 A1 Dec. 28, 2006

(51) Int. Cl.
*C07K 16/00* (2006.01)
*C12N 15/09* (2006.01)

(52) U.S. Cl. .............. 530/388.15; 435/69.1; 435/320.1; 435/325; 435/7.1; 536/23.5

(58) Field of Classification Search ........................ None
See application file for complete search history.

(56) References Cited

U.S. PATENT DOCUMENTS

| | | | |
|---|---|---|---|
| 4,732,863 | A | 3/1988 | Tomasi et al. |
| 5,695,760 | A | 12/1997 | Faanes et al. |
| 5,994,511 | A | 11/1999 | Lowman et al. |
| 6,290,957 | B1 | 9/2001 | Lowman et al. |
| 7,138,501 | B2 * | 11/2006 | Ruben et al. ........... 530/388.23 |
| 2001/0024831 | A1 | 9/2001 | Der Maur et al. |
| 2002/0054878 | A1 | 5/2002 | Lowman et al. |
| 2002/0128450 | A1 | 9/2002 | Nishida et al. |
| 2003/0096306 | A1 | 5/2003 | Maur et al. |
| 2003/0103978 | A1 * | 6/2003 | Deshpande et al. ...... 424/152.1 |
| 2003/0149244 | A1 | 8/2003 | Lowman et al. |

FOREIGN PATENT DOCUMENTS

| | | |
|---|---|---|
| CN | 1267307 | 9/2000 |
| EP | 0 974 600 A2 | 1/2000 |
| JP | 05-304987 | 11/1993 |
| JP | 2000-236884 (A) | 9/2000 |
| WO | WO-99/09063 | 2/1999 |
| WO | WO-00/56771 A1 | 9/2000 |
| WO | WO 01/58956 A2 | 8/2001 |
| WO | WO 01/62285 A1 | 8/2001 |
| WO | WO 01/62932 A1 | 8/2001 |
| WO | WO 03/076472 A2 | 9/2003 |

OTHER PUBLICATIONS

Ignatovich et al., "Dominance of Intrinsic Genetic Factors in Shaping the Human Immunoglobulin $V_\lambda$ Repertoire", J. Mol. Biol. 294:457-465 (1999).
Soos, "Identification of natural antibodies to interleukin-18 in the sera of normal humans and three nonhuman primate species", Clinical Immunology, 109:188-196 (2003).
Haruki Okamura et al., "Cloning of a New Cytokine that includes IFN- y Production by T cells", Nature, vol. 378:88-91 (Nov. 2, 1995).
Tomohiro Yoshimoto et al., "Interleukin 18 together with Interleukin 12 Inhibits IgE Production by Induction of Interferon- y Production from Activated B Cells", Proc. Natl. Acad. Sci. USA, vol. 94:3948-3953 (Apr. 1997).
Kenji Nakanishi et al., "Interleukin-18 Regulates Both TH1 and TH2 Responses", Annu. Rev. Immunol. 19:423-474 (2001).
Tomohiro Yoshimoto et al., "IL-18, Although Antiallergic When Administered with IL-12, Stimulates IL-4 and Histamine Release by Basophils", PNAS, 96(24):13962-13966(Nov. 23, 1999).
Tomohiro Yoshimoto et al., "IL-18 Induction of IgE: Dependence on $CD4^+$ T cells, IL-4 and STAT6", Nature Immunology, 1(2):132-137 (Aug. 2000).
Tomohiro Yoshimoto et al., "Nonredundant Roles for CD 1 d-Restricted Natural Killer T Cells and Conventional $CD4^+T$ Cells in the Induction of Immunoglobulin E Antibodies in Response to Interleukin 18 Treatment of Mice", The Journal of Experimental Medicine, 197(8):997-1005 (Apr. 21, 2003).
Hiroshi Konishi et al., "IL-18 Contributes to the Spontaneous Development of Atopic Dermatitis-Like Inflammatory Skin Lesion Independently of IgE/stat6 under Specific Pathogen-Free Conditions", PNAS, 99(17):11340-11345 (Aug. 20, 2002).
Yong GU et al., "Activation of Interferon- y Inducing Factor Mediated by Interleukin-1 (3 Converting Enzyme", Science, 275: 206-209 (Jan. 10, 1997).
Kei-ichi Yamanaka et al., "Skin-Specific Caspase-I-Transgenic Mice Show Cutaneous Apoptosis and pre-Endotoxin Shock Condition with a High Serum Level of IL-18", The Journal of Immunology, pp. 997-1003 (2000).

(Continued)

*Primary Examiner*—Dong Jiang
(74) *Attorney, Agent, or Firm*—Edwards Angell Palmer & Dodge LLP; David G. Conlin; Jonathan M. Sparks

(57) ABSTRACT

A human-derived human anti-human IL-18 antibody of the present invention is an antibody against human IL-18, the antibody including: an H-chain complementarity determining region consisting of (a) a polypeptide consisting of amino-acid sequences represented by SEQ ID NOS: 4 to 6, or (b) a polypeptide which is a mutant of the polypeptide (a) and which serves as the H-chain complementarity determining region; and an L-chain complementarity determining region against human interleukin-18 consisting of (c) a polypeptide consisting of amino-acid sequences represented by SEQ ID NOS: 10 to 12, or (d) a polypeptide which is a mutant of the polypeptide (c) and which serves as the L-chain complementarity determining region. This makes it possible to provide a human anti-human IL-18 antibody and a method for using the antibody.

28 Claims, 13 Drawing Sheets

OTHER PUBLICATIONS

Kiyoshi Takeda et al., "Essential Role of Stat6 in IL-4 Signalling", Nature, 380(6575):627-630(Apr. 18, 1996).

Hiroko Tsutsui et al., "IL-18 Accounts for Both TNF- a—and Fas Ligand-mediated Hepatotoxic pathways in Endotoxin-Induced Liver Injury in Mice", The Journal of Immunology, pp. 3961-3967(1997).

Hiroko Tsutsui et al., "Caspase-1-Independent, Fas/Fas Ligand-Mediated IL-18 Secretion from Macrophages Causes Acute Liver Injury in Mice", Immunity, 11:359-367 (Sep. 1999).

Hiroko Tsutsui et al., Pathophysiological Roles of Interleukin-18 in Inflammatory Liver Diseases, Immunological reviews, 174:, 192-209 (2000).

Shau-ping LEI et al., "Characterization of the *Erwinia carotovora pelB* Gene and its Product Pectate Lyase", Journal of Bacteriology, pp. 4379-4383 (Sep. 1987).

Takahiro Fukumoto et al., "Peptide Mimics of the CTLA4-Binding Domain Stimulate T -Cell Proliferation", Nature Biotechnology, 16:267-270 (Mar. 1998).

Takaaki Sugimoto et al., "Interleukin 18 Acts on Memory T Helper Cells Type 1 to Induce Airway Inflammation and Hyperresponsiveness in a Naive Host Mouse", J. Exp. Med., 199(4):535-545 (Feb. 16, 2004).

Henry Milgrom, et al., "Treatment of Allergic Asthma with Monoclonal Anti-IgE Antibody", the New England Journal of Medicine, 341(26):1966-1973 (Dec. 23, 1999).

James D. Marks et al., "By-passing Immunization Human Antibodies from V -gene Libraries Displayed on Phage", J. Mol. Biol., 222:581-597 (1991).

Kouji Tominaga et al., "IL-12 Synergizes with IL-18 or IL-1 (3 for IFN- y Production from human T Cells", International Immunology, 12(2):151-160 (2000).

Yuji Ito et al., Human Antibody Engineering for Molecular Targeting Therapy,: Bio Industry, Jul. 2003, pp. 34-42.

Eric Tse et al., "Intracellular Antibody Capture Technology: Application to Selection of Intracellular Antibodies Recognising the BCR-ABL Oncogenic Protein," J. Mol. Biol., vol. 317, 2002, pp. 85-94.

M. Taniguchi et al., "Characterization of anti-human interleukin-18 (IL-18)/interferon-y-inducing factor (IGIF) monoclonal antibodies and their application in the measurement of human IL-18 by ELISA", Journ. of Immun. Meth., vol. 206, pp. 107-113 (1997).

* cited by examiner

SEQUENCE LISTING

```
<160> NUMBER OF SEQ ID NOS: 12

<210> SEQ ID NO 1
<211> LENGTH: 357
<212> TYPE: DNA
<213> ORGANISM: Homo sapiens

<400> SEQUENCE: 1
caggtgcagc tggtgcagtc tggggctgag gtgaggaggc ctggggcctc agtgagggtt      60
tcctgcaagg catctggata caccttcact agtcactata tacactgggt gcgacaggcc     120
cctggacaag ggcttgagtg ggtggcaata atcaaccccta gtgatggcag aacagactac    180
gcacagaagt tccagggcag agtcaccgtg accagggaca cgtccgcgag cagtgtctac    240
atgggaataa gcagcctgag atctgaggac acggccatgt attactgtgc gagaacagcg    300
cgtggattca gttatgcgac agactggggc cagggaaccc tggtcaccgt ctcctca       357

<210> SEQ ID NO 2
<211> LENGTH: 357
<212> TYPE: DNA
<213> ORGANISM: Homo sapiens
<220> FEATURE:
<221> NAME/KEY: CDS
<222> LOCATION: (1)..(357)

<400> SEQUENCE: 2 cag gtg cag ctg gtg cag tct ggg gct gag gtg agg agg cct ggg gcc       48
Gln Val Gln Leu Val Gln Ser Gly Ala Glu Val Arg Arg Pro Gly Ala
 1               5                  10                  15 tca gtg agg gtt tcc tgc aag gca tct gga tac acc ttc act agt cac       96
Ser Val Arg Val Ser Cys Lys Ala Ser Gly Tyr Thr Phe Thr Ser His
            20                  25                  30 tat ata cac tgg gtg cga cag gcc cct gga caa ggg ctt gag tgg gtg      144
Tyr Ile His Trp Val Arg Gln Ala Pro Gly Gln Gly Leu Glu Trp Val
        35                  40                  45 gca ata atc aac cct agt gat ggc aga aca gac tac gca cag aag ttc      192
Ala Ile Ile Asn Pro Ser Asp Gly Arg Thr Asp Tyr Ala Gln Lys Phe
    50                  55                  60 cag ggc aga gtc acc gtg acc agg gac acg tcc gcg agc agt gtc tac      240
Gln Gly Arg Val Thr Val Thr Arg Asp Thr Ser Ala Ser Ser Val Tyr
65                  70                  75                  80 atg gga ata agc agc ctg aga tct gag gac acg gcc atg tat tac tgt      288
Met Gly Ile Ser Ser Leu Arg Ser Glu Asp Thr Ala Met Tyr Tyr Cys
                85                  90                  95 gcg aga aca gcg cgt gga ttc agt tat gcg aca gac tgg ggc cag gga      336
Ala Arg Thr Ala Arg Gly Phe Ser Tyr Ala Thr Asp Trp Gly Gln Gly
```

```
                        100                 105                 110
acc ctg gtc acc gtc tcc tca                                              357
Thr Leu Val Thr Val Ser Ser
        115

<210> SEQ ID NO 3
<211> LENGTH: 119
<212> TYPE: PRT
<213> ORGANISM: Homo sapiens

<400> SEQUENCE: 3

Gln Val Gln Leu Val Gln Ser Gly Ala Glu Val Arg Arg Pro Gly Ala
  1               5                  10                  15

Ser Val Arg Val Ser Cys Lys Ala Ser Gly Tyr Thr Phe Thr Ser His
             20                  25                  30

Tyr Ile His Trp Val Arg Gln Ala Pro Gly Gln Gly Leu Glu Trp Val
         35                  40                  45

Ala Ile Ile Asn Pro Ser Asp Gly Arg Thr Asp Tyr Ala Gln Lys Phe
     50                  55                  60

Gln Gly Arg Val Thr Val Thr Arg Asp Thr Ser Ala Ser Ser Val Tyr
 65                  70                  75                  80

Met Gly Ile Ser Ser Leu Arg Ser Glu Asp Thr Ala Met Tyr Tyr Cys
                 85                  90                  95

Ala Arg Thr Ala Arg Gly Phe Ser Tyr Ala Thr Asp Trp Gly Gln Gly
            100                 105                 110

Thr Leu Val Thr Val Ser Ser
        115

<210> SEQ ID NO 4
<211> LENGTH: 5
<212> TYPE: PRT
<213> ORGANISM: Homo sapiens

<400> SEQUENCE: 4

Ser His Tyr Ile His
  1               5

<210> SEQ ID NO 5
<211> LENGTH: 17
<212> TYPE: PRT
<213> ORGANISM: Homo sapiens

<400> SEQUENCE: 5

Ile Ile Asn Pro Ser Asp Gly Arg Thr Asp Tyr Ala Gln Lys Phe Gln
  1               5                  10                  15

Gly

<210> SEQ ID NO 6
<211> LENGTH: 10
<212> TYPE: PRT
<213> ORGANISM: Homo sapiens

<400> SEQUENCE: 6

Thr Ala Arg Gly Phe Ser Tyr Ala Thr Asp
  1               5                  10

<210> SEQ ID NO 7
<211> LENGTH: 327
<212> TYPE: DNA
<213> ORGANISM: Homo sapiens
```

-continued

```
<400> SEQUENCE: 7
tcctatgagc tgactcagcc accctcggtg tcagtgtccc caggacaaac ggccaggatc    60
acctgctctg gagatgcatt gccaaaaaaa tatgcttatt ggtaccagca gaagccaggc   120
caggcccctg tgctggtgat atataaagac agtgagaggc cctcagggat ccctgagcga   180
ttctctggct ccagctcagg gacaacagtc acgttgacca tcagtggagt ccaggcagaa   240
gacgaggctg actattactg tcaatcagca gacagcagtg gtacttatgt ggtattcggc   300
ggagggaccc agctcaccgt tttaggt                                       327

<210> SEQ ID NO 8
<211> LENGTH: 327
<212> TYPE: DNA
<213> ORGANISM: Homo sapiens
<220> FEATURE:
<221> NAME/KEY: CDS
<222> LOCATION: (1)..(327)

<400> SEQUENCE: 8 tcc tat gag ctg act cag cca ccc tcg gtg tca gtg tcc cca gga caa      48
Ser Tyr Glu Leu Thr Gln Pro Pro Ser Val Ser Val Ser Pro Gly Gln
 1               5                  10                  15 acg gcc agg atc acc tgc tct gga gat gca ttg cca aaa aaa tat gct      96
Thr Ala Arg Ile Thr Cys Ser Gly Asp Ala Leu Pro Lys Lys Tyr Ala
             20                  25                  30 tat tgg tac cag cag aag cca ggc cag gcc cct gtg ctg gtg ata tat     144
Tyr Trp Tyr Gln Gln Lys Pro Gly Gln Ala Pro Val Leu Val Ile Tyr
         35                  40                  45 aaa gac agt gag agg ccc tca ggg atc cct gag cga ttc tct ggc tcc     192
Lys Asp Ser Glu Arg Pro Ser Gly Ile Pro Glu Arg Phe Ser Gly Ser
     50                  55                  60 agc tca ggg aca aca gtc acg ttg acc atc agt gga gtc cag gca gaa     240
Ser Ser Gly Thr Thr Val Thr Leu Thr Ile Ser Gly Val Gln Ala Glu
 65                  70                  75                  80 gac gag gct gac tat tac tgt caa tca gca gac agc agt ggt act tat     288
Asp Glu Ala Asp Tyr Tyr Cys Gln Ser Ala Asp Ser Ser Gly Thr Tyr
                 85                  90                  95 gtg gta ttc ggc gga ggg acc cag ctc acc gtt tta ggt                 327
Val Val Phe Gly Gly Gly Thr Gln Leu Thr Val Leu Gly
             100                 105

<210> SEQ ID NO 9
<211> LENGTH: 109
<212> TYPE: PRT
<213> ORGANISM: Homo sapiens

<400> SEQUENCE: 9

Ser Tyr Glu Leu Thr Gln Pro Pro Ser Val Ser Val Ser Pro Gly Gln
 1               5                  10                  15

Thr Ala Arg Ile Thr Cys Ser Gly Asp Ala Leu Pro Lys Lys Tyr Ala
             20                  25                  30

Tyr Trp Tyr Gln Gln Lys Pro Gly Gln Ala Pro Val Leu Val Ile Tyr
         35                  40                  45

Lys Asp Ser Glu Arg Pro Ser Gly Ile Pro Glu Arg Phe Ser Gly Ser
     50                  55                  60

Ser Ser Gly Thr Thr Val Thr Leu Thr Ile Ser Gly Val Gln Ala Glu
 65                  70                  75                  80

Asp Glu Ala Asp Tyr Tyr Cys Gln Ser Ala Asp Ser Ser Gly Thr Tyr
                 85                  90                  95
```

-continued

```
Val Val Phe Gly Gly Gly Thr Gln Leu Thr Val Leu Gly
            100                 105

<210> SEQ ID NO 10
<211> LENGTH: 11
<212> TYPE: PRT
<213> ORGANISM: Homo sapiens

<400> SEQUENCE: 10

Ser Gly Asp Ala Leu Pro Lys Lys Tyr Ala Tyr
  1               5                  10

<210> SEQ ID NO 11
<211> LENGTH: 7
<212> TYPE: PRT
<213> ORGANISM: Homo sapiens

<400> SEQUENCE: 11

Lys Asp Ser Glu Arg Pro Ser
  1               5

<210> SEQ ID NO 12
<211> LENGTH: 11
<212> TYPE: PRT
<213> ORGANISM: Homo sapiens

<400> SEQUENCE: 12

Gln Ser Ala Asp Ser Ser Gly Thr Tyr Val Val
  1               5                  10
```

HUMAN ANTI-HUMAN INTERLEUKIN-18 ANTIBODY, FRAGMENT THEREOF AND METHOD FOR USING SAME

TECHNICAL FIELD

The present invention relates to a human anti-human interleukin-18 antibody, a fragment thereof, and a method for using the antibody and fragment. More particularly, the present invention relates to a human anti-human IL-18 antibody that binds to interleukin-18 (hereinafter referred to as "IL-18") and that inhibits physiological activity of IL-18, a fragment of the antibody, and a method for using the antibody and fragment. The antibody and the fragment thereof are expected to serve as therapeutic drugs for inflammation or immune abnormality disease caused by IL-18.

BACKGROUND ART

Atopic dermatitis (AD) refers to an inflammatory skin lesion caused mainly by an external stimulus, and is accompanied by chronic repetitive intense itching. The mechanism of AD development is poorly understood. However, it is understood that AD development has a genetic background. The serum of an AD patient contains a high level of IgE. Further, activated T cells, basophils, and mast cells are deeply involved in the mechanism of AD development. Particularly, these cells are activated when IgE. molecules binding to Fcε receptors (FcεR) on the mast cells or the basophils are cross-linked by allergens. As a result, Th2 cytokines (i.e., cytokines derived from type 2 helper T (Th2) cells) and chemical mediators (derived from the Th2 cells) are produced. It is supposed that this causes AD development. Important examples of the Th2 cytokines are IL-4, IL-5, IL-9, and IL-13. Important examples of the chemical mediators are histamine, serotonin, and leukotriene.

When helper T (Th) cells are antigenically stimulated, the Th cells produce the cytokines. Based on patterns in which the helper T cells produce the cytokines, the Th cells are categorized into two subgroups: Th1 cells and Th2 cells. When the type 1 helper T (Th1) cells are stimulated, the Th1 cells produce Th1 cytokines such as IFN-γ, IL-2, and TNF-β. When the type 2 helper T (Th2) cells are stimulated, the Th2 cells produce Th2 cytokines such as IL-4, IL-5, IL-10, and IL-13. The Th1 cells mainly induce cellular immunity, and the Th2 cells induce humoral immunity and sometimes induce an allergic response. When naive T cells are antigenically stimulated in the presence of IL-12, the naive T cells are differentiated into Th1 cells. When the naive T cells are antigenically stimulated in the presence of IL-4, the naive T cells are differentiated into Th2 cells.

IL-18, immediately after its discovery, drew attention as a factor inducing T cells and NK (natural killer) cells to produce IFN-γ (Okamura, H. et al. *Nature* 378, 88 (1995).). However, IL-18 must coexist with IL-12 before it can exert such a function (Nakanishi, K. et al., *Annu. Rev. Immunol.*, 19, 423 (2001)). Further, INF-γ, which is a type of Th1 cytokine, blocks the action of IL-4, which is a type of Th2 cytokine. Therefore, it was supposed that IL-18, which induces IFN-γ, suppresses an immune response and exhibits an antiallergic action.

When a mouse is infected with a parasite, Th2 cells are induced and IgE is produced. The inventors has revealed that administering IL-12 and IL-18 to the mouse right after the infection induces IFN-γ production from the T cells, NK cells, and B cells and thereby suppresses IgE production (Yoshimoto, T. et al., *Proc. Natl. Acad. Sci. USA.*, 94, 3948 (1997)).

Furthermore, the inventors have also revealed that administering only IL-18 increases IgE production (Yoshimoto, T. et al., *Proc. Natl. Acad. Sci. USA.*, 96, 13962 (1999)). Further, a subsequent analysis has revealed that administering IL-18 to a healthy mouse induces IgE production (Yoshimoto, T. et al., *Nat. Immunol.*, 1, 132 (2000)).

IL-18 administered into a living organism acts on CD4 positive T cells ($CD4^+$ T cells) to induce expression of a CD40 ligand (CD40L) and production of IL-4, IL-5, IL-13, and the like (Yoshimoto, T. et al., *J. Exp. Med.*, 197, 997 (2003)). Further, B cells produce IgE when the B cells are stimulated in vivo by CD40L and IL-4. The CD40L was expressed by the IL-18-stimulated CD4 positive T cells.

IL-18 in vitro acts on basophils and mast cells, both of which are induced by IL-3, to induce production of IL-4, IL-13, histamine, and the like (Konishi, H. et al., *Proc. Natl. Acad. Sci. USA*, 99, 11340 (2002)).

According to a conventionally accepted theory, as described in the beginning, it has been held that mast cells are activated when allergens bind to a plurality of IgE molecules binding through Fc sites to FcεR on the mast cells and thereby cross-link these IgE molecules. Although this accepted theory still hold true, the inventors have revealed that even in the absence of an allergen and IgE, IL-18 directly activates mast cells and basophils to induce production of IL-4, IL-13, histamine, and the like (Yoshimoto, T. et al., *Proc. Natl. Acad. Sci. USA.*, 96, 13962 (1999)). Also in such a case, allergic inflammation occurs.

IL-18 is produced as a biologically inactive precursor (IL-18 precursor), activated when cleaved by caspase 1, and then secreted extracellularly (Gu, Y. et al., *Science*, 275, 206 (1997)). The inventors found that IL-18 precursors are produced and accumulated in cutaneous keratinocytes. Based on this finding, the inventors produced a mouse (caspase 1 transgenic mouse) in which caspase 1 is overexpressed specifically in cutaneous keratinocytes (Yamanaka, K. et al., *J. Immunol.*, 165, 997 (2000)). As a result, in the mouse, a large amount of biologically active IL-18 was produced. Further, in the mouse blood, a large amount of IgE was produced (Yoshimoto, T. et al., *Nat. Immunol,.* 1, 132 (2000), Konishi, H. et al., *Proc. Natl. Acad. Sci. USA*, 99, 11340 (2002)). Furthermore, although the mouse was grown in an allergen-free environment, the mouse developed intense atopic dermatitis (Konishi, H. et al., *Proc. Natl. Acad. Sci. USA*, 99, 11340 (2002).

Incidentally, it has become clear that IL-4 and IL-13 exert their actions when their respective signals are transmitted through Stat6 into the nucleus of a targeted cell. The inventors have revealed that IgE is not produced in a Stat6-deficient mouse (Takeda, K. et al., *Nature*, 380, 627 (1996)). Moreover, the inventors mated the caspase 1 transgenic mouse with such a Stat6-gene-deficient mouse so as to produce a Stat6-gene-deficient caspase 1 transgenic mouse. As a result, the inventors found that the Stat6-gene-deficient caspase 1 transgenic mouse developed intense atopic dermatitis, even though the mouse produce no IgE (Konishi, H. et al., *Proc. Natl. Acad. Sci. USA*, 99, 11340 (2002)).

Meanwhile, the inventors mated the caspase 1 transgenic mouse with an IL-18-gene-deficient mouse so as to produce an IL-18-deficient caspase 1 transgenic mouse. It was found as a result that the IL-18-deficient caspase 1 transgenic mouse had a large amount of IgE in the blood, even though IgE production was suppressed. However, in the mouse, although IgE was produced, the development of atopic dermatitis was completely. suppressed (Konishi, H. et al., *Proc. Natl. Acad. Sci. USA*, 99, 11340 (2002)).

From these results, it can be said that atopic dermatitis can-be treated more effectively by inhibiting the action of IL-18 than by suppressing IgE production.

Immediately after its discovery, IL-18 was called an INF-γ inducing factor. As the name implies, IL-18 acts on the Th1 cells or NK cells synergically with IL-12 so as to strongly induce INF-γ production (Okamura, H. et al. *Nature* 378, 88 (1995)., Nakanishi, K. et al., *Annu. Rev. Immnuol.*, 19, 423 (2001)). Furthermore, IL-18 enhances expression of a Fas ligand (FasL) on these cells (Tsutsui, H. et al., *J. Immnuol.*, 159, 3961 (.1997)). When FasL is a trimer, FasL induces cell apoptosis.

The inventors have reported that Fas is expressed by Kupffer cells that exist in the liver of a mouse to which Propionibacterium acnes has been administered, and that FasL stimulates the Kupffer cells to produce active IL-18 (Tsutsui, H. et al., *Immunity*, 11, 359 (1999)). Furthermore, IL-18 acts on the NK cells and Th1 cells to enhance FasL expression. Thus, it has become clear that there is a positive correlation (positive feedback loop) between IL-18 and FasL (Tsutsui, H. et al., *J. Immunol.*, 159, 3961 (1997), Tsutsui, H. et al., *Immunity*, 11, 359 (1999), Tsutsui, H. et al., *Immunol. Rev.*, 174, 192 (2000)). Therefore, it has become clear that when IL-18 is overproduced in vivo, serious damage to the liver and intestine is caused. As these findings show, IL-18 also causes so-called Th1 diseases.

It has been suggested that IL-18 is also involved in Th1- cell-induced bronchial asthma and other diseases, as well as the diseases named above.

As described above, controlling production or activity of IL-18 plays an extremely important role in a method for treating IL-18-dependent disease or Th1 disease. A typical example of the IL-18 dependent disease is IL-18-dependent atopic dermatitis. The Th1. disease is a type of disease developed or exacerbated due to overproduction of IL-18.

Therefore, if a specific monoclonal antibody that neutralizes the physiological activity of IL-18 were developed, such a monoclonal antibody would serve as a means of effectively treating many types of IL-18-related diseases.

In reality, only a few mouse- and rat-derived monoclonal antibodies have been obtained as antibodies against human IL-18 (anti-human IL-18 antibodies) (For example, Japanese Unexamined Patent Publication No. 236884/2000 (*Tokukai* 2000-236884; published on Sep. 5, 2000), International Application No. WO00/56771 (published on Sep. 28, 2000).

However, the conventional anti-human IL-18 antibodies are mostly monoclonal antibodies derived from nonhuman animals, and when such antibodies are administered to a human, the antibodies are recognized as foreign substances and rejected as such. Therefore, it is difficult to use the conventional anti-human IL-18 antibodies as therapeutic drugs for human-IL-18-related diseases. Particularly, because the antibodies are administered continuously for a prolonged time period in order to treat autoimmune disease, this raises such a problem that antibodies are produced against the administered antibodies.

This problem may be solved by biogenetically humanizing the mouse anti-human -IL-18 monoclonal antibodies.

However, while humanization of the mouse monoclonal antibodies reduces antigenicity, there is a possibility that, when the humanized anti-human IL-18 antibodies are administered to a chronic autoimmune disease patient repeatedly or for a prolonged time period, antibodies (blocking antibodies) are produced which block activity of the humanized IL-18 antibodies. As a result, a remarkable therapeutic effect is not achieved. In some cases, there is a possibility that some serious side effects are produced.

Therefore, there is a strong demand for development of an anti-human IL-18 antibody that ensures a high level of safety even when administered repeatedly or for a prolonged time period.

The present invention has been made in view of the foregoing problems and has as an object to provide (i) a human anti-human interleukin-18 antibody which assures safety and a therapeutic effect and (ii) a fragment thereof, and to propose (iii) a method for using the antibody and fragment.

DISCLOSURE OF INVENTION

The inventors of the present invention diligently studied in view of the foregoing problems. That is, the inventors obtained single-chain variable region (scFv) molecules (antibody fragments) of a fully human anti-human IL-18 antibody from a phage display library expressing genes, prepared from peripheral blood B lymphocytes of healthy persons, which code immunoglobulin H- and L-chain variable regions ($V_H$ and $V_L$). As a result, the inventors have identified (i) respective amino-acid sequences of the antibody fragments and (ii) cDNA base sequences for coding for the amino-acid sequences. Thus, the inventors have completed the present invention.

The present invention includes, as medically and industrially useful methods and substances, the following features (A) to (X).

(A) A human anti-human interleukin-18 antibody against human interleukin-18.

(B) The human anti-human interleukin-18 antibody according to (A), including: an H-chain complementarity determining region consisting of (a) a polypeptide consisting of amino-acid sequences represented by SEQ ID NOS: 4 to 6, or (b) a polypeptide consisting of amino-acid sequences, represented by SEQ ID NOS: 4 to 6, one or more amino acids of which are substituted, deleted, inserted, and/or added, and which serves as the H-chain complementarity determining region against human interleukin-18; and an L-chain complementarity determining region consisting of (c) a polypeptide consisting of amino-acid sequences represented by SEQ ID NOS: 10 to 12, or (d) a polypeptide consisting of amino-acid sequences, represented by SEQ ID NOS: 10 to 12, one or more amino acids of which are substituted; deleted, inserted, and/or added, and which serves as the L-chain complementarity determining region against the human interleukin-18.

(C) The human anti-human interleukin-18 antibody according to (A) or (B), including:. an H-chain variable region consisting of (e) a polypeptide consisting of an amino-acid sequence represented by SEQ ID NO: 3, or (f) a polypeptide consisting of an amino-acid sequence, represented by SEQ ID NO: 3, one or more amino acids of which are substituted, deleted, inserted, and/or added, and which serves as the H-chain variable region against the human interleukin-18; and an L-chain variable region consisting of (g) a polypeptide consisting of an amino-acid sequence represented by SEQ ID NO: 9, or (h) a polypeptide consisting of an amino-acid sequence, represented by SEQ ID NO: 9, one or more amino acids of which are substituted, deleted, inserted, and/or added, and which serves as the L-chain variable region against human interleukin-18.

(D) An H-chain variable region fragment of a human-derived antibody (human anti-human IL-18 antibody) against human interleukin-18, the fragment consisting of (e) a polypeptide consisting of an amino-acid sequence represented by SEQ ID. NO: 3, or (f) a polypeptide consisting of an amino-acid sequence, represented by SEQ ID NO: 3, one or more amino acids of which are substituted, deleted, inserted, and/or added, and which serves as an H-chain variable region against human interleukin-18.

(E) An L-chain variable region fragment of a human-derived antibody against human interleukin-18, the fragment consisting of (g) a polypeptide consisting of an amino-acid sequence represented by SEQ ID NO: 9, or (h) a polypeptide consisting of an amino-acid sequence, represented by SEQ ID NO: 9, one or more amino acids of which are substituted, deleted, inserted, and/or added, and which serves as an L-chain variable region against human interleukin-18.

(F) A single-chain variable region fragment of a human-derived antibody against human interleukin-18, the fragment including: (1) an H-chain variable region fragment including the H-chain complementarity determining region according to (B), or (2) the H-chain variable region fragment according to (D); and (3) an L-chain variable region fragment including the L-chain complementarity determining region according to (B), or (4) the. L-chain variable region fragment according to (E), the H-chain variable region fragment and the L-chain variable region fragment being ligated to each other.

(G) A human-derived antibody against human interleukin-18, or a fragment thereof, the antibody or fragment including: (1) an H-chain variable region fragment including the H-chain complementarity determining region according to (B), or (2) the H-chain variable region fragment according to (D); and/or (3) an L-chain variable region fragment including the L-chain complementarity determining region according to (B), or (4) the L-chain variable region fragment according to (E), the H-chain variable region fragment and/or the L-chain variable region fragment being ligated to a human-derived constant region.

(H) The fragment according to (G), which comprises an Fab fragment, an Fab' fragment, an $F(ab')_2$ fragment, an scAb fragment, or an scFvFc fragment.

(I) A modified antibody, including the antibody according to any one of (A) to (H), or the fragment thereof, and a modification agent binding thereto.

(J) A gene coding for either (1) the antibody according to any one of (A) to (H), or (2) the fragment thereof.

(K) The gene according to (J), including as an open reading frame region a base sequence represented by SEQ ID NO: 1 or 7.

(L) A recombinant expression vector including the gene according to (J) or (K).

(M) A transformant, including the gene according to (J) or (K) introduced therein.

(N) A method for producing either (1) a human-derived human anti-human interleukin-18 antibody, or (2) a fragment thereof, by causing a host to express the gene according to (J) or (K).

(O) A detector for interleukin-18, the detector using (1) the antibody according to any one of (A) to (H), (2) the fragment thereof, or (3) the modified antibody according to (I).

(P) A diagnostic kit for measuring an amount of human interleukin-18 contained in a test sample, the diagnostic kit using a detecting reagent including (1) the antibody according to any one of Claims (A) to (H), (2) the fragment thereof, or (3) the modified antibody according to (I).

(Q) A method for diagnosing immunological disease in accordance with an amount of human interleukin-18 contained in a test sample and measured by using the detecting reagent according to (P).

(R) A human interleukin-18 activity inhibitor, including a human interleukin-18 antagonist as an active ingredient.

(S) The human interleukin-18 activity inhibitor according to (R), wherein the human interleukin-18 antagonist is any one of following substances selected from:
(i) the human anti-human interleukin-18 antibody according to any one of (A) to (C);
(ii) the fragment according to any one (D) to (H);
(iii) the modified antibody according to (I); and
(iv) a low-molecular compound obtained through molecular designing in accordance with an antigen determining region on human interleukin-18, the antigen determining region being recognized by (1) the antibody according to (i), (2) the antibody fragment according to (ii), or (3) the modified antibody according to (iii).

(T) A gene therapy agent, including the gene according to (J) or (K).

(U) An immunological disease treatment agent, including either (1) the human interleukin-18 activity inhibitor according to (R) or (S), or (2) the gene therapy agent according to (T).

(V) A method for treating immunological disease by administering the immunological disease treatment agent according to (U).

(W) The immunological disease treatment agent according to (U), which inhibits cytokines produced from helper T1 cells stimulated with an antigen and human interleukin-18.

(X) The immunological disease treatment agent according to (U) or (W), which is applied to human interleukin-18-related allergy, inflammation, and chronic immune abnormality disease.

The present invention makes it possible to provide (i) a human-derived anti-human IL-18 antibody, (ii) a fragment thereof, and (iii) a method for using the antibody and fragment, instead of a chimera antibody or humanized antibody thus far provided. Therefore, the present invention makes it possible to provide a therapeutic drug that exhibits a remarkable therapeutic effect and a high level of safety even when administered repeatedly or for a prolonged time period in treatment of disease caused directly or indirectly by IL-18.

Additional objects, features, and strengths of the present invention will be made clear by the description below. Further, the advantages of the present invention will be evident from the following explanation in reference to the drawings.

BEST MODE FOR CARRYING OUT THE INVENTION

Figure 1:
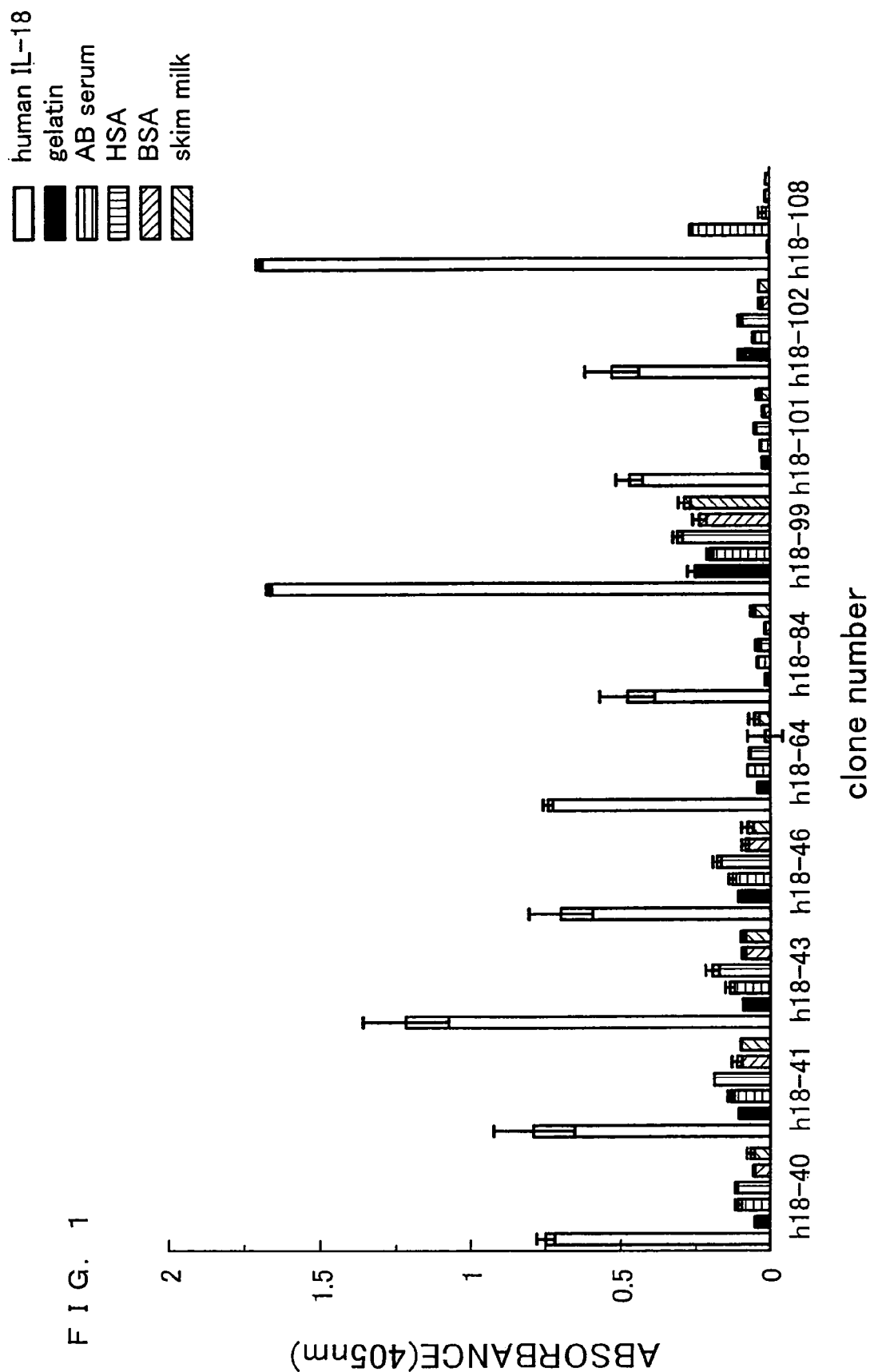
FIG. 1 is a graph showing respective specificities, which are evaluated by ELISA, of cloned scFv fragments, which are separated in Example 1, with respect to human IL-18.

One embodiment of the present invention is described below. The present invention is not to be limited to the following embodiment.

(1) An Antibody of the Present Invention and a Fragment Thereof

The inventors of the present invention studied a human anti-human interleukin-18 (IL-18) antibody against human IL-18. As a result, the inventors have revealed that a human-derived single-chain variable region fragment (scFv fragment) obtained through a phage display method inhibits human IL-18 from inducing signal transduction and INF-γ production. Furthermore, the inventors identified, in the single-chain variable region fragment (scFv), (i) a complementarity determining region (CDR), (ii) respective amino-acid sequences of H-chain and L-chain variable regions, and (iii) respective base sequences of genes coding for the amino-acid sequences.

SEQ ID NO: 3 represents an amino-acid sequence of a $V_H$ chain. SEQ ID NOS: 4 to 6 respectively represent amino-acid sequences of complementarity determining regions (CDRs 1 to 3) in the $V_H$ chain. That is, in the $V_H$-chain amino-acid sequence represented by SEQ ID NO: 3, the 31st to 35th amino-acid sequences, the 50th to 66th amino-acid sequences, and the 99th to 108th amino-acid sequences correspond to CDR1 (SEQ ID NO: 4), CDR2 (SEQ ID NO: 5), and CDR3 (SEQ ID NO: 6), respectively.

Meanwhile, SEQ ID NO: 9 represents an amino-acid sequence of a $V_L$ chain. SEQ ID NOS: 10 to 12 respectively represent amino-acid sequences of complementarity determining regions (CDRs 1 to 3) in the $V_L$ chain. That is, in the $V_L$-chain amino-acid sequence represented by SEQ ID NO: 9, the 33rd amino-acid sequence, the 49th to 55th amino-acid sequences, and the 88th to 98th amino-acid sequences correspond to CDR1 (SEQ ID NO: 10), CDR2 (SEQ ID NO: 11), and CDR3 (SEQ ID NO: 6), respectively.

An antibody of the present invention and a fragment thereof are not limited to the $V_H$ chain, the $V_L$ chain, and the CDRs of the $V_H$ and $V_L$ chains as represented by the sequences of SEQ ID NOS: 3 to 6 and 9 to 12, but may be mutated polypeptides obtained by partially altering the sequences.

That is, the CDR of the $V_H$ chain includes not only (a) a polypeptide consisting of an amino-acid sequence represented by any one of SEQ ID NOS: 4 to 6, but also (b) a polypeptide consisting of an amino-acid sequence, represented by any one of SEQ ID NOS: 4 to 6, one or more amino acids of which are substituted, deleted, inserted, and/or added, and which serves as an H-chain complementarity determining region against human interleukin-18.

Meanwhile, the CDR of the $V_L$ chain includes not only (c) a polypeptide consisting of an amino-acid sequence represented by any one of SEQ ID NOS: 10 to 12, but also (d) a polypeptide consisting of an amino-acid sequence, represented by any one of SEQ ID NOS: 10 to 12, one or more amino acids of which are substituted, deleted, inserted, and/or added, and which serves as an L-chain complementarity determining region against human interleukin-18.

Further, the $V_H$-chain variable region includes not only (e) a polypeptide consisting of an amino-acid sequence represented by SEQ ID NO: 3, but also (f) a polypeptide consisting of an amino-acid sequence, represented by any one of SEQ ID NO: 3, one or more amino acids of which are substituted, deleted, inserted, and/or added, and which serves as the H-chain complementarity determining region against human interleukin-18.

Similarly, the $V_H$-chain variable region includes not only (g) a polypeptide consisting of an amino-acid sequence represented by SEQ ID NO: 9, but also (h) a polypeptide consisting of an amino-acid sequence, represented by any one of SEQ ID NO: 9, one or more amino acids of which are substituted, deleted, inserted, and/or added, and which serves as an L-chain complementarity determining region against human interleukin-18.

As the phrase is used herein, "one or more amino acids of which are substituted, deleted, inserted, and/or added" means substitution, deletion, insertion, and/or addition of amino acids allowed by a publicly-known mutant protein producing method such as site-directed mutagenesis. Therefore, for example, the polypeptide (b) is a mutant peptide of the polypeptide (a). As the term is used herein, the "mutation" primarily means mutation artificially introduced in accordance with the publicly-known mutant protein producing method, but may also mean a mutant obtained by isolating and purifying the same kind of mutant peptide that exists in nature (e.g., a human).

When the antibody of the present invention and the fragment thereof are used as therapeutic drugs as described later (when they are administered to a human), the "mutation" is carried out in so far as an immune response is not caused in a human-derived structure or in a human. When the antibody of the present invention and the fragment thereof are used as detectors or diagnostic kits (when they are not administered to a human), the "mutation" is not particularly limited. Further, when the antibody of the present invention and the fragment thereof are administered to a human, the "mutation" is preferably carried out in so far as the higher-order structure of CDR that recognizes an antigen is maintained.

Further, the antibody of the present invention and the fragment thereof may include an additional peptide. Such a polypeptide is added, for example, when a protein of the present invention is epitope-labeled by His, Myc, Flag, or the like.

Since the CDR is a region that recognizes an antigen, a complementarity determining region (CDR) of the antibody of the present invention or that of the fragment thereof recognizes human IL-18. Therefore, the $V_H$ chain and the $V_L$ chain need to include at least the CDRs of the $V_H$ and $V_L$ chains, and the remaining regions may consist of amino-acid sequences of human-derived $V_H$ and L chains. This makes it possible to maintain specificity for human IL-18. However, the CDR is specifically constructed in accordance with the primary and higher-order structures of the H- and L-chain variable regions. For this reason, an anti-human IL-18 antibody arranged so as to include the human-derived $V_H$ and L chains in addition to at least the CDRs of the $V_H$ and $V_L$ chains has specificity for human IL-18. For example, an antibody having specificity for human IL-18 can be produced by maintaining at least the higher-order structure of the CDR.

More specifically, an antibody of the present invention and the fragment thereof are of human origin. Examples of the antibody of the present invention and the fragment thereof are shown in (I) to (IV) as follows.

(I) A $V_H$ chain including the H-chain complementarity determining region according to (a) or (b).
(II) A $V_H$ chain consisting of the polypeptide of (e) or (f).
(III) A $V_L$ chain including the L-chain complementarity determining region according to (c) or (d).
(IV) A $V_L$ chain consisting of the polypeptide of (g) or (h).
(V) A single-chain variable region fragment (scFv fragment) including the $V_H$ chain of (I) or (II) ligated to the $V_L$ chain of (III) or (IV).
(VI) A fragment including the $V_H$ chain of (I) or (II) and/or the $V_L$ chain of (III) of (IV), the $V_H$ chain and/or the $V_L$ chain being ligated to a human-derived constant region.

In (v) and (vi), the $V_H$ chain and the $V_L$ chain are ligated to each other normally through an appropriate peptide linker. An example of the peptide linker is an arbitrary single-chain peptide consisting of 10 to 25 amino-acid residues.

Further, the fragment according to (vi) including the $V_H$ chain and/or the $V_L$ chain ligated to the human-derived constant region may be an scAb fragment, an Fab fragment, an Fab' fragment, an F(ab')$_2$ fragment, an scAb fragment having at least part of an Fc site, an scFvFc fragment, or a complete antibody. The scAb fragment is obtained by binding an scFv fragment to a domain (C domain) that occupies part of an L- or H-chain constant region. The scFvFc fragment is obtained by binding an scFv fragment to all H- and L-chain constant regions.

Furthermore, in order to improve safety and antibody value, the antibody of the present invention and the fragment thereof may include a modification agent binding thereto. That is, the antibody of the present invention and the fragment thereof may be modified antibodies. Examples of the modification agent are a sugar chain and a polymer. When the sugar chain is used as the modification agent, the sugar chain may exhibit some sort of physiological. When such a simple polymer as polyethyleneglycol (PEG) is used as the modification agent, the simple polymer does not exhibit physiological activity by itself. Furthermore, polyethyleneglycolating the antibody of the present invention and the fragment thereof may inhibit the antibody and the fragment from being absorbed by the liver, or may stabilize the antibody and the fragment in the blood. That is, a preferred example of the modification agent is a simple polymer such as PEG.

As with the production of the mutant peptide, when the antibody of the present invention and the fragment thereof are used as therapeutic drugs, they can be modified by the modification agent in so far as an immune response is not caused in a human. When the antibody of the present invention and the fragment thereof are used as detectors or diagnostic kits, the way in which the antibody and the fragment are modified by the modifier agent is not particularly limited. Further, when the antibody of the present invention and the fragment thereof are administered to a human, they are preferably modified in so far as the higher-order structure of CDR that recognizes an antigen is maintained.

Further, the antibody embraces a protein structurally associated with the antibody. That is, the antibody means an immunoglobulin. Furthermore, the antibody of the present invention may be classified as IgA, IgD, IgE, IgG, or IgM. In other words, the antibody of the present invention may be a monomer or a multimer such as a dimer, a trimer, a tetramer, or a pentamer.

As described later in Examples, the scFv fragment was analyzed in detail. As a result, as described later in detail in Examples, the scFv fragment was found to behave as follows.
[1] The scFv fragment binds specifically to human IL-18.
[2] The scFv fragment inhibits human IL-18 from inducing signal transduction and INF-γ production.

Thus, since the scFv fragment has a human-derived amino-acid sequence, formation of an inhibitory antibody for inhibiting activity of an antibody is highly unlikely. Furthermore, the scFv fragment binds firmly to human IL-18 so as to inhibit physiological activity of human IL-18. Therefore, the scFv fragment inhibits human IL-18 from causing various immune responses. Therefore, the scFv fragment and an antibody including the scFv fragment, or a fragment of the antibody, can be used to treat disease in which human IL-18 is directly or indirectly involved. Examples of such disease are allergy, inflammation, and chronic immune abnormality disease. If such a therapeutic drug were developed, it would be possible to establish a new method for treating a human-IL-18-related disease.

(2) A Gene According to the Present Invention

A gene according to the present invention is a gene for coding for the antibody described in section (1) or the fragment thereof. The gene includes (i) a gene including as an open reading frame (ORF) region a base sequence represented by SEQ ID NO: 1 or 7; and an altered gene including the base sequence part of which is altered.

Since the gene codes for the antibody of the present invention or the fragment thereof, the antibody of the present invention, or the fragment thereof, can be expressed by introducing the gene into an appropriate host (e.g., bacteria or yeast).

Furthermore, the "gene" may include not only a sequence for coding for the antibody of (1) or the fragment thereof but also a sequence such as an untranslated region (UTR) sequence or a vector sequence (including an expression vector sequence). For example, the gene of the present invention may be arranged by connecting to the vector sequence the sequence according to SEQ ID NO: 1 or 7. Then, by amplifying the gene of the present invention in an appropriate host, the gene can be amplified in a desired manner. Further, a partial sequence of the gene of the present invention may be used as a probe. Further, as described later, the gene of the present invention can be used as a gene therapy agent (gene therapy drug) for human-IL-18-related disease.

(3) Methods for Obtaining and Producing the Antibody of the Present Invention and the Fragment Thereof As described later in Examples, the antibody of (1) and the fragment thereof can be obtained for example by using a so-called phage display method. Further, the antibody of (1) and the fragment thereof can be produced by causing a host to express the gene described in section (2). The methods for obtaining and producing an antibody and a fragment thereof are not to be limited to those described herein.

More specifically, mRNA is extracted from peripheral blood B lymphocytes of healthy persons, and $V_H$- and $V_L$ chains of an immunoglobulin gene are amplified according to an RT-PCR method by using a primer pair that define both ends of each chain. As a result, H- and L-chain V region populations having various sequences are obtained. Next, (i)

DNA coding for a peptide linker and (ii) a primer pair so defined as to ligate one end of the DNA with the H chain and the other end with the L chain are amplified together. As a result, various scFv DNA populations having random combinations of H- and L-chain V regions are prepared. The scFv DNA thus obtained is incorporated into a phagemid vector pCANTAB5E, so as to prepare an scFv display phage library. The library is allowed to react with human IL-18 immobilized on a plastic tube. Unreacted scFv display phage is washed away. Thereafter, an scFv phage clone binding to human IL-18 is eluted with acid. From the phage clone thus separated, scFv DNA is prepared. The scFv DNA is incorporated into an expression vector. The expression vector is used to transform a host. The host is cultured according to an ordinary method. As a result, only targeted scFv protein is obtained.

SEQ ID NOS: 1 and 7 represent base sequences of cDNA that codes for the $V_H$ and $V_L$ chains of the anti-human IL-18 single-chain variable region (scFv fragment) obtained in accordance with the phage display antibody method.

The scFv DNA can be expressed, for example, in *Escherichia coli*. Use of *Escherichia coli* makes it possible to express scFv functionally combined with a useful common promoter, a signal sequence for antibody secretion, and the like. Examples of the promoter are a lacZ promoter and an arab promoter. The signal sequence for scFv secretion may be a pelB signal sequence (Lei, S P., et al, *J. Bacteriol.*, 1987, 169: 4379-4383), if scFv is to be expressed in the periplasm of *Escherichia coli*. A signal sequence of g3 protein of an M13 phage can be used for causing scFv secretion in a culture supernatant.

The scFv fragment thus expressed can be separated from inside and outside of the host cell so as to be purified homogeneously. The scFv fragment expressed in the present invention has an E tag sequence added to the C terminus. Therefore, the scFv fragment can be easily and quickly purified by using affinity chromatography using the anti E tag antibody. Alternatively, the scFv fragment can be purified by using a combination of methods for separating and purifying normal protein. For example, the antibody can be separated and purified by using a combination of ultrafiltration, salting out, and column chromatography (e.g., gel filtration chromatography, ion-exchange column chromatography, or hydrophobic interaction chromatography).

The scFv protein (polypeptide) thus obtained was shown to have binding activity for human IL-18, as will be described later in Examples. Examples of a method for measuring the antigen-binding activity of the human anti-human IL-18 antibody of the present invention are ELISA and BIAcore. For example, when ELISA is used, a sample including a target anti-IL-18 antibody or antibody fragment is placed on a 96-well plate having human IL-18 immobilized thereon. An example of the sample is an *Escherichia coli* culture supernatant or a purified antibody. Next, to the plate, a secondary antibody labeled with an enzyme such as alkaline phosphatase is added. The plate is incubated and washed. Thereafter, to the plate, chromogenic substrate para-nitrophenyl phosphate is added, and an absorbance of the chromogenic substrate is measured. In this way, the antigen-binding activity can be evaluated.

Furthermore, it has become clear that the scFv protein obtained -according to the present invention dose-dependently inhibits human IL-18 from inducing human marrow mononuclear KG-1 cells to produce IFN-γ.

Therefore, since the scFv protein inhibits biological activity of human IL-18, the scFv protein is expected to effectively prevent or treat disease caused by the action of IL-18.

(4) A Recombinant Expression Vector and the Like of the Present Invention

A recombinant expression vector of the present invention includes the gene of (2). That is, the recombinant vector includes the gene coding for either (i) the antibody of (1) or (ii) the fragment thereof. An example of the recombinant expression vector is a recombinant expression vector that includes cDNA having a base sequence represented by SEQ ID NO: 1 or 7. The recombinant expression vector can be produced by using any of plasmid, phage, cosmid, etc.

Thus, the recombinant expression vector includes the gene of the present invention. The vector is particularly limited as long as a vector capable of being expressed in a host cell is appropriately selected. That is, in order to ensure gene expression, a promoter sequence is appropriately selected in accordance with a type of host cell, and an expression vector is obtained by incorporating the promoter sequence and the gene of the present invention into the plasmid or the like.

A variety of markers may be used in order to check whether or not the gene of the present invention has been introduced into the host cell, and whether or not the gene is properly expressed in the host cell. For example, a gene missing in the host cell is used as a marker, and the plasmid or the like including the marker and the gene of the present invention is introduced as the expression vector into the host cell. This makes it possible to confirm the introduction of the gene of the present invention based on the expression of the marker gene. Alternatively, the antibody according to the present invention, or the fragment thereof, may be expressed as a fusion protein. For example, a green fluorescent protein (GFP) derived from *Aequorea voctoria* is used as a marker, and the antibody according to the present invention, or the fragment thereof, may be expressed as a GFP fusion protein.

Suitable examples of the host cell include, but are not limited to, a variety of conventional publicly-known cells. Specifically, when the gene of (2) is full length DNA, examples of the host cell include, but are not limited to, animal cells such as human- or mouse-derived cells, oocytes of *Caenorhabditis elegans* or *Xenopas laevis*, cultured cells of various mammals (such as rats, rabbits, pigs, and monkeys), or cultured cells of various insects (e.g., fruit flies and bombycids). Examples of the host cell used when the gene of (2) is a DNA fragment include, but are not limited to, bacteria (e.g., *Escherichia coli*) or yeast (e. g., *Saccharomyces cerevisiae* or *Schizosaccharomyces pombe*).

The expression vector may be introduced into the host cell by any of a variety of conventional publicly-known methods such as a transformation method an electroporation method, a calcium phosphate. precipitation method, a liposome method, a DEAE dextran method, etc.

A transformant of the present invention includes the gene of (2) introduced therein, the gene coding for either (i) the antibody of (1) or (ii) the fragment thereof. As used herein, "the gene introduction" means that the gene is introduced into a targeted cell (host cell) according to a publicly-known genetic engineering technique (genetic manipulation technique) so as to be expressed in the targeted cell. Further, the "transformant", as used herein, embraces not only cells, tissues, and organs but also individual animals. Examples of a targeted animal include, but are not limited to, mammals such as cows, pigs, sheep, goats, dogs, cats, guinea pigs, hamsters, mice, rats, etc. Particularly, rodents such as mice and rats are widely used as laboratory animals and animal models of disease. Among them, mice are preferably used as laboratory animals and animal models of disease for a variety of reasons. A first reason is that a large number of inbred mice are available. A second reason is that techniques of, for example, culturing a fertilized egg and a technique for in vitro fertilization are well established for mice. For example, knockout mice are very useful in further analyzing the function of the antibody or the fragment thereof, developing a method for diagnosing human IL-18-related disease, and developing a method for treating the disease.

The antibody of (1), or the fragment thereof, can be produced by using the transformant of the present invention produced by using the recombinant expression vector of the present invention.

(5) A Method for Using the Antibody of the Present Invention and the Fragment Thereof (5-1) A Human -IL-18 Detector, a Kit for Diagnosing Immunological Disease, and a Diagnostic Method The antibody of (1), the fragment thereof, or the modified antibody strongly binds specifically to human IL-18, and therefore can be used to detect and measure human IL-18. That is, a human IL-18 detector makes it possible, for example, to highly precisely detect human IL-18 contained in a sample such as blood or urine. Therefore, the human IL-18 detector can be used as a diagnostic and therapeutic tool for identifying human-IL-18-related disease and evaluating the therapeutic effect.

The human IL-18 detector of the present invention uses at least an amino-acid sequence of a CDR in the antibody of the present invention. The human IL-18 detector can be used to detect and measure IL-18 under various conditions. An example of the human IL-18 detector is an antibody chip, an antibody column, or the like, in which the antibody of the present invention or the fragment thereof, binding specifically to human IL-18, is immobilized on a substrate (carrier).

Further, the antibody of the present invention, or the fragment thereof, is very useful in purifying human IL-18 by means of immuno affinity chromatography. This purification method includes the steps of: causing the antibody of the present invention, or the fragment thereof, to absorb human IL-18 by bringing the antibody or the fragment into contact with a mixture of human IL-18 and other substances; and desorbing and extracting the absorbed human IL-18 from the antibody or the fragment. The purification method makes it possible to purify IL-18 both quickly and highly precisely.

The antibody of the present invention, or the fragment thereof, and the modified antibody of the antibody and the modified antibody of the fragment are widely applicable to a reagent (human IL-18 detecting reagent) for detecting human IL-18. That is, when a labeling immunoassay (e.g., a radio immunoassay, an enzyme assay, or a fluorescent immunoassay) using these antibodies or the fragments thereof is applied, human IL-18 contained in a test sample can be qualitatively or quantitatively analyzed both quickly and accurately. In this labeling immunoassay, the antibodies or the fragments thereof are labeled for example by a radioactive substance, an enzyme, and/or a fluorescent substance before use. Further, these antibodies or the fragments thereof react specifically to human IL-18 and exhibits an immuno response. Therefore, when the immuno response is measured by using the labeling substance as an index, it is possible to precisely detect a small quantity of human IL-18 contained in the test sample. As compared with a bioassay, the labeling immunoassay makes it possible to analyze a large number of test samples at a time and reduce time and labor required for analysis, and allows for highly precise analysis.

A kit of the present invention for diagnosing immunological disease and a method of the present invention for diagnosing immunological disease make it possible to measure an amount of human IL-18 contained in a test sample (e.g., blood, body fluid, or tissue), in accordance with such a method for detecting human IL-18. The diagnostic kit and the diagnostic method also make it possible to diagnose immunological disease in accordance with the measurement result. The "Immunological disease", as used herein, refers to human-IL-18-related disease. Examples of immunological disease include atopic dermatitis, airway inflammation, airway hyperresponsiveness (AHR), and asthma.

Thus, the detecting method using the human IL-18 detector of the present invention is useful in process management and quality control in producing human IL-18. Further, the kit of the present invention for diagnosing immunological disease and the diagnostic method of the present invention are very useful in diagnosing sensitivity disease with a level of human IL-18 contained in tissue or body fluid used as an index, and in evaluating treatment of various types of immunological diseases.

Antibodies commonly used for diagnostic purposes are produced by immunizing a nonhuman animal such as a mouse, a rabbit, or a goat. However, in the animal immune system, lymphocytes that produce antibodies binding to molecules constituting the animal are either eliminated or deactivated. That is, the anti-human IL-18 antibodies produced by immunizing animals do not include antibodies in which the antigen determining region is similar between human IL-18 and animal IL-18.

In contrast, the antibody of the present invention is an antibody screened from the phage library presenting the human anti-human IL-18 antibody. Unlike in the case of animals, this phage does not have a mechanism for eliminating or deactivating antibodies. Therefore, the antibody of the present invention includes an anti IL-18 antibody that cannot be produced by immunizing an animal and that has binding specificity to an antigen determining region common to IL-18 of various animals such as humans, monkeys, etc. When such an antibody is used for the detector of the present invention or the diagnostic kit of the present invention, it is possible to diagnose IL-18-related disease in a variety of animal models of disease such as monkeys as well as humans.

(5-2) Human IL-18 Activity Inhibitor and the Like

The antibody of (1) is a human anti-human IL-18 antibody that specifically recognizes human IL-18. Further, the antibody binds specifically to human IL-18. The antibody inhibits human IL-18 from binding to a receptor, so that signal transduction through the receptor is inhibited. Thus, the antibody inhibits human IL-18 from inducing IFN-γ production.

Therefore, in other words, the antibody is a human IL-18 antagonist. The human IL-18 antagonist can be used as a human interleukin-18 activity inhibitor.

Examples of the "human IL-18 antagonist" include, but are not limited to, the following substances (i) to (iv).

(i) An antibody of (1) according to the present invention.
(ii) A fragment of the antibody of (1) according to the present invention.
(iii) A modified antibody of the antibody of (1) according to the present invention, or the fragment thereof.
(iv) A low-molecular compound obtained through molecular designing based on an antigen determining region on human IL-18, the antigen determining region being recognized by the antibody of (i), the fragment (ii), or the modified antibody of (iii).

The "human interleukin-18 activity inhibitor", as used herein, may be an inhibitor that inhibits the activity of human interleukin-18, an inhibitor that competitively inhibits human interleukin-18 from binding to a receptor, or an inhibitor that binds to a complex of-human IL-18 and the IL-18 receptor so as to inhibit signal transduction.

Further, the gene of (2) according to the present invention can be used as a gene therapy agent for treating human-IL-18-related immunological disease. Ingestion of the gene therapy agent causes the antibody of the present invention, or the fragment thereof, to be formed in vivo. Therefore, the gene therapy agent brings about the same effect as the human IL-18 activity inhibitor. When anti-human IL-18 antibodies continue to be formed in vivo, the action of human IL-18 is excessively inhibited. However, in a human body, IL-1 exhibits the same action as IL-18. Therefore, there is no problem even if IL-18 is deficient.

The antibody of the present invention is human-derived human anti-human IL-18 that specifically recognizes human IL-18. That is, the antibody is different from a conventional chimera antibody or humanized antibody, and amino-acid sequences of the antibody are all of human origin.

Therefore, there is no possibility of forming an antibody (inhibitor antibody) that blocks the action of the antibody of the present invention. Thus, even when the antibody is administered repeatedly or for a prolonged time period, the antibody can continue to be effective while retaining a high level of safety.

Therefore, the human IL-18 activity inhibitor of the present invention and the gene therapy agent of the present invention can be used as an immunological disease treatment agent (immune therapy drug) useful as a method for treating human-IL-18-related immunological disease.

The immunological disease treatment agent of the present invention exhibits its effect in vivo. Therefore, the immunological disease treatment agent of the present invention may be achieved either (1) by administering a polypeptide consisting of an amino-acid sequence of SEQ ID NO: 3 (or a human IL-18 activity inhibitor including the polypeptide), or (2) by expressing the polypeptide through the metabolism of a prodrug in vivo. That is, the immunological disease treatment agent of the present invention may be achieved by using a prodrug made from either (I) any one of the human IL-18 antagonists of (i) to (iv), or (II) the gene therapy agent. That is, the immunological disease treatment agent may be modified so as to become an active metabolite in vivo.

The immunological disease treatment agent of the present invention may include a pharmaceutically acceptable additive. Examples of the additive include at least one type of diluent, at least one type of binder, at least one type of disintegrator, at least one type of lubricant, at least one type of buffer, etc.

As described above, the antibody (human monoclonal antibody) of the present invention and the fragment molecule thereof have variable regions of a human-derived anti-human IL-18 antibody, react strongly with human IL-18, and inhibit IL-18 from binding to an IL-18 receptor. Furthermore, the antibody and the fragment molecule can inhibit a variety of immuno responses caused by IL-18, and can be used as a drug for preventing or treating allergy, inflammation, and immune abnormality disease caused by the immuno responses. An example of such a drug is an antiinflammatory agent or a drug for treating or preventing autoimmune disease.

Further, the human-derived scFv fragment of the present invention against human IL-18 has been shown to bind specifically to IL-18 and to inhibit IL-18 from inducing signal transduction and IFN-γ production. Therefore, the scFv fragment and the human anti-human IL-18 antibody, or the fragment thereof, in which the $V_H$ and $V_L$ chains of the scFv fragment bind to a human constant region or part thereof, are expected to be applied to treatment of IL-18-related disease (e.g., chronic inflammatory disease or autoimmune disease). Further, an antibody that binds to IL-18 but does not exhibit an inhibitory effect, as well as the antibodies that bind to IL-18 and exhibits an inhibitory effect, can be used to measure a concentration of IL-18 contained in blood and to monitor a change in pathologic condition.

As described above, the antibody of the present invention inhibits IL-18 from inducing signal transduction and IFN-γ production. Therefore, if an antigen determining region that exhibits binding specificity to both ah antibody having such characteristics and the human IL-18 were identified on IL-18, then it would be possible to apply a low-molecular compound to the development of a drug for treating immunological disease. Such an antigen determining region is called an epitope. The epitope may be a primary amino-acid sequence itself. Alternatively, the epitope may be a conformation constructed depending on how peptide chains are folded. In either case, an epitope-like compound (mimic molecule) can be designed, for example, in accordance with "Molecular Template Design Method Using a Monoclonal Antibody" proposed by the inventors of the present invention (T. Fukumoto et al., *Nature Biotechnology,* 16:267-270, 1998.). As the term is used herein, the "low-molecular compound" does not refers to a compound (e.g., a peptide or an antibody) whose molecular weight is relatively high (molecular weight of 10000 or higher). Instead, it refers to a compound that is used generally as a low-molecular pharmaceutical product and that has a molecular weight of less than 10000 or preferably 3000. The lower the molecular weight of the low-molecular compound, the more preferred the low-molecular compound is.

A peptide or a compound having an even lower molecular weight can be produced through an in silico process, in order to produce the low-molecular compound. In the in silico process, molecular design is carried out by focusing attention on the molecular structure of the mimic molecule. Thus, by carrying out the molecular design in silico, a low-molecular compound capable of serving as a therapeutic drug can be inexpensively and quickly selected as a lead compound.

Specifically, for example in Examples described later, CDRs of a human anti-human IL-18 scFv antibody are represented by. SEQ ID NOS: 4 to 6 and SEQ ID NOS: 10 to 12. Generally, a CDR of an antibody is a region (site) that recognizes an antigen. That is, the CDR serves as an active center of the antibody. That is, an scFv fragment shown in Example 1 has a CDR that specifically recognizes human IL-18. Therefore, when a low-molecular compound is designed so as to correspond substantially (preferably completely) to a higher-order structure of the CDR, the low-molecular compound can be used as a low-molecular pharmaceutical product. In other words, the low-molecular compound is designed so as to resemble a conformation of the CDR. The in silico process is not particularly limited. For example, the in silico process can be designed on a computer. The silico process can be designed based on a CDR's functional group and the CDR's higher-order structure. The silico process can be designed in accordance with SBDD (structure-based drug design), CADD (computer-aided drug design), or the like.

The low-molecular compound thus designed is more stable than a protein (peptide) such as an antibody. Therefore, the low-molecular compound can be used as an easy-to-handle pharmaceutical product.

(5-3) Application of the Immunological Disease Treatment Drug: Case 1

As described above, the human IL-18 activity inhibitor of the present invention and the gene therapy agent of the present invention serve as an immunological disease treatment drug useful as a method for treating human-IL-18-related disease. Described below is a case in which the immunological disease treatment drug is applied.

Th1-dominant immune responses have been generally considered for the pathology of autoimmune disease but are protective against Th2-related disease (asthma, atopy, etc.). However, recent studies revealed that Th1 cells are involved in augmenting Th2-related airway hypersensitivity. Furthermore, the Th1 cells are shown to induce airway hyperresponsiveness (AHR) by increase and activation of neutrophils.

Indeed, the airways of asthmatic patients are associated with increased levels of IFN-γ, TNFα, and IL-8 as well as an increased number of neutrophils. Nevertheless, it is yet to be understood how the Th1 cells counteract Th2 cells and exhibit such pathological capacity. Thus, it is important to understand the pathological involvement of the Th1 cells to induction of airway inflammation and hyperresponsiveness.

IL-18 was originally identified as a factor that enhances IFN-γ production of Th1 cells in the presence of an anti-CD3 antibody and IL-12. Therefore, injection of a mixture of IL-12 and IL-18 induces IFN-γ producing cells in vivo and thereby inhibits a Th2-induced IgE response. However, the inventors have revealed in their recent study that when a naive host mouse (nonsensitized host mouse) into which in vitro induced antigen-specific Th1 or Th2 cells have been passively transferred is left untreated for approximately one month, the transferred Th1 or Th2 cells become memory phenotype Th1 or Th2 cells, and that the host animal: develops airway inflammation when the Th1 or Th2 cells are stimulated with either a nasally administered antigen or an antigen plus IL-18 (T. Sugimoto et al., *J. EXP. Med.*, 2004, 199, 535-545.). According to previous reports, neutralization of IL-13 inhibits eosinophilic infiltration and AHR in Th2 cell-transferred mice. In contrast, the same treatment cannot inhibit AHR in Th1 cell-transferred mice, even though this treatment remarkably reduces airway eosinophilic infiltration.

These results suggest that the Th1 cells induce AHR in an entirely different manner from the Th2 cells. The Th1 cells exhibit very unique responses to stimulation caused by an antigen and IL-18, and, produce Th1 cytokines (INF-γ), Th2 cytokines (IL-9, IL-13), chemokines (RANTES, MIP-1α (macrophage-derived inflammatory protein-1α)), and GM-CSF). It is widely accepted that the Th2 cytokines and GM-CSF are principally responsible for inducing bronchial asthma. Several studies suggested that the Th1 and Th2 cells do not inhibit each other but rather cooperate to induce development of bronchial asthma and augment a symptom of bronchial asthma. Indeed, concurrent administration of IFN-γ and IL-13 induces the most severe bronchial asthma. The inventors found a novel function of the Th1 cells. That is, when stimulated with an antigen and IL-18, the Th1 cells produce the Th1 cytokines, the Th2 cytokines, GM-CSF, and the chemokines so as to induce various inflammatory pathologic conditions.

Therefore, human Th1 cells may also become pathological under the same condition.

In Example 2 described later, it was confirmed that human Th1 cells produce Th1 cytokines, Th2 cytokines, GM-CSF, and chemokines in the presence of an antigen and IL-18. In this Example, it has been revealed that newly induced Th1 cells, which strongly express IL-18Rα, remarkably increase production of IFN-γ, IL-13, GM-CSF, and IL-8 upon stimulation with an anti-CD3 antibody and IL-18. These results suggest the possibility of the Th1 cells inducing tissue injuries by production of GM-CSF and IL-8, as well as by production of the Th1 and Th2 cytokines.

Thus, IL-18 cooperates with an antigen to stimulate the Th1 cells, with the result that severe airway inflammation and AHR are developed. Therefore, for example, the foregoing human IL-18 antagonists (as defined in (i) to (iv)) serve as therapeutic drugs for the types of disease.

(5-4) Application of the Immunological Disease Treatment Drug: Case 2

Described below is another case in which the immunological disease treatment drug is applied.

Atopic dermatitis has been considered so far as allergen-specific IgE-antibody-dependent acquired atopy. Therefore, an IgE antibody inhibitor, an antiallergic agent, and the like that are targeted at an allergen-specific IgE antibody has been used as therapeutic drugs for atopic dermatitis. However, the number of patients who cannot be treated, or suffers from a relapse, even with these therapeutic drugs, has been yearly increasing.

IL-18 is highly responsible for development and severity of natural atopy, which cannot by treated by a therapeutic drug for acquired atopic dermatitis (IgE antibody-dependent atopic dermatitis).

However, no method for effectively treating such disease has been established.

The Th1 cells, which are antagonistic to the function of Th2 cells, can be induced by a method such as CpGDNA administration. However, the IL-18, induced at the same time, acts on the Th1 cells and undesirably induces TH1-type bronchial asthma.

An antigen-specific hypersensitization therapy is known to be a method for treating acquired atopic dermatitis (IgE-antibody-dependent atopic dermatitis). However, since the molecular mechanism of the disease is yet to be understood, the effectiveness of the therapy is low. The hypersensitization therapy is a treatment method in which an allergen is administered in vivo (generally injected), so that hypersensitive reactions against the allergen are reduced. The allergen serves as an antigen responsible for an IgE-antibody-related immediate allergic reaction (I-type allergic reaction). A particular example of the allergen is an inhalent allergen.

It has been reported that Genetic Inc. has developed a human murine antibody that is specific to an Fc site of an IgE antibody and that inhibits the IgE antibody from binding to an FcR1 site, and that the human murine antibody is effective as a drug for cancer treatment (Milgrom H. et al., *N. Engl. J. Med.*, 1999:341, 1966-73.).

Further, a Th2 cytokine inhibitor may be capable of serving as an antibody drug (pharmaceutical product) for treating allergy. Examples of the Th2 cytokine inhibitor are an anti IL-4 antibody, an anti IL-5 antibody, an anti IL-13 antibody, an antibody against a receptor for IL-4, an antibody against a receptor for IL-5, and an antibody against a receptor for IL-13. However, no effective antibody drug has been developed.

It has been reported that a low dose of a low-molecular immunosuppressive drug typified by FK506 exerts an anti-allergic effect, but produces a side effect such as renal involvement.

CpGDNA has drawn attention as means that induces IL-12 production when stimulated with TLR (Toll Like Receptor). CpGDNA is DNA having a nonmethylated CpG motif. CpGDNA is principally responsible for a Th1 response (macrophage-activating response). CpGDNA is a molecule that is expected to be applied in a clinical setting. However, as described above, CpGDNA poses such a problem that the concurrently induced IL-18 acts on the Th1 cells and induces TH1-type bronchial asthma.

As described above, since atopic disease has been considered as allergen-specific IgE-dependent acquired atopic disease, an IgE inhibitor and an anti-allergic agent that are targeted at the acquired atopic disease have been used as therapeutic drugs. However, the number of patients who cannot be treated, or suffers from a relapse, even with the use of these therapeutic drugs, has been yearly increasing.

That is, there exists natural atopy that cannot be treated by a conventional treatment method targeted at acquired atopy. In the development of natural atopy, IL-18 plays an important role.

Conventional immunology has held that Th1 cell induction inhibits Th2 cell functions so as to exert an antiallergic effect. However, the inventors have found that IL-18 produces INF-γ, IL-8, IL-9, IL-13, and the like by stimulating Th1 cells under in vivo conditions, and then induces intractable bronchial asthma. This disproves an established theory holding that allergic inflammation is developed due to an unbalance between Th1 cells and Th2 cells. That is, this clearly denies a conventional treatment method aimed at correcting such an unbalance.

IL-4, IL-5, IL-9, and IL-13 are important Th2 cytokines. Leukotriene, histamine, serotonin, and the like are important chemical mediators. There is a technique for individually suppressing (inhibiting) such cytokines; however, the technique does not make it possible to inhibit the cytokine from being produced upstream. That is, there is a technique for suppressing (inhibiting) a function of the cytokine by directly acting on the cytokine; however, there is no technique for inhibiting the cytokine from being produced upstream. Since IL-18 presides upstream of the cytokine, inhibition of the activity of IL-18 is effective in treating allergic disease (allergic inflammation).

In the mechanism for developing allergic disease, activated T cells, basophils, and mast cells are deeply involved. Particularly, these cells are activated when IgE molecules binding to Fcε receptors on the mast cell or basophils are cross-linked by allergens. As a result, the Th2 cytokines and the chemical mediators are produced, so that allergic inflammation (allergic disease) is induced. However, there are cases where allergic inflammation is induced because of infection, not because of the allergens and IgE. There is a non-specific treatment method such as an anti-allergic agent or an immunosuppressive agent. However, no technique for specifically suppressing IL-18 has been developed.

A conventional anti-IL-18 antibody is produced by humanizing a murine antibody, and therefore cannot serve as an antibody drug capable of clinical applications.

The antibody of the present invention is a human-derived human anti-human IL-18 monoclonal antibody (fully human antibody) against IL-18, which induces natural atopy (IL-18-dependent disease). Conventionally, no fully human antibody against human IL-18 has been developed, and the antibody of the present invention is the only antibody in the world to serve as such. Unlike the murine antibody, the antibody of the present invention does not become antigenic even when applied in a clinical setting. Therefore, the antibody of the present invention can be used as an excellent antibody drug having no side effect. This makes it possible to establish a novel method for treating allergic disease, natural atopy, asthma, and the like. For example, the antibody of the present invention can be established as a novel treatment method targeted at natural atopy (IL-18-dependent), which cannot be treated by using the conventional treatment method targeted at acquired atopic disease (IgE-dependent) caused by abnormalities in an acquired immune system.

As described later in Examples, the antibody of the present invention inhibited activity of IL-18 in various in vitro systems. Particularly, the antibody of the present invention has a function of inhibiting Th1 cells from producing Th1 cytokines and Th2 cytokines, when the Th1 cells are stimulated with an antigen-and IL-18. The function is important in that an effect of IL-12 is not impaired.

Therefore, the foregoing immunological disease treatment drug plays an important role as a therapeutic target for allergic inflammation, which is one type of current intractable disease. Furthermore, the foregoing immunological disease treatment drug is useful in producing a novel type of therapeutic drug totally different from a conventional drug for treating allergic inflammation.

As-described above, IL-18 stimulates the Th1 cells so as to induce bronchial asthma.

Further, IL-18 is produced not only from immune cells such as a dendritic cell and a -macrophage, but also from nonimmune cells such as a cutaneous keratinocyte, an intestinal epithelial cell, and a tracheal epithelial cell.

Further, in the presence of IL-12, IL-18 induces the various immune or nonimmune cells to produce IFN-γ. Meanwhile, in the absence of IL-12, IL-18 induces NKT cells, T cells, and NK cells to produce Th2 cytokines (cytokines produced from helper T2 cells) such as IL-4 and IL-13, and thereby antigen-nonspecifically induces IgE production.

Further, IL-18 stimulates antigen-stimulated Th1 cells so as to increase the production of IFN-γ, which is a type of Th1 cytokine, and to induce the production of IL-9 and IL-13, which are types of Th2 cytokine, and IL-8, which is a typical type of chemokine.

Further, IL-18 can induce Th1-type bronchial asthma when nasally administered together with OVA (when IL-18 and OVA are administered) to a mouse into which OVA-specific Th1-type memory T cells are implanted. Th1-type bronchial asthma is characterized by (i) a high level of neutrophilic, lymphocytic, macrophage, and eosinophilic infiltration in alveoli and interstitium and (ii) airway hyperresponsiveness.

Further, IL-18 directly stimulates mast cells and basophils antigen/IgE-independently. As a result, IL-18 induces the production of various cytokines and chemical mediators and induces natural atopy (IL-18-dependent inflammation).

Th2-cell-dependent asthma can be suppressed by using an anti-IL-5 antibody or an anti-IL-13 antibody. However, these antibodies are ineffective in treating asthma induced by Th1 cells stimulated with an antigen and IL-18. The antibody of the present invention is effective in treating asthma that cannot be treated by using the foregoing antibodies. That is, the antibody of the present invention is effective against IL-18-induced asthma (asthma that is developed due to infection).

The present invention plays an important role in (i) detecting IL-18-related asthma and (ii) establishing a novel treatment method targeted at natural atopy (IL-18-dependent), which cannot be treated by using the conventional treatment method targeted at acquired atopy (IgE-dependent) caused by abnormalities in an acquired immune system.

Further, the antibody of the present invention is an anti-human IL-18 antibody (human IL-18 monoclonal human antibody against human IL-18) that plays an important role in binding a natural immune system to an acquired immune system.

The antibody of the present invention provides a novel treatment method targeted at natural atopy (IL-18-dependent), which cannot be treated by using the conventional treatment method targeted at acquired atopy (IgE-dependent) caused by abnormalities in an acquired immune system.

Furthermore, the antibody of the present invention provides a novel method for treating atopic dermatitis, asthma, nasal inflammation, and other types of allergic disease. Particularly, IL-18 stimulates Th1 cells so as to develop intractable bronchial asthma. For this reason, pathogens that infect respiratory epithelia and that induce tracheal epithelial cells to produce IL-18 can cause development of bronchial asthma. Therefore, the antibody of the present invention serves as an effective therapeutic drug for asthma developed due to infection.

The antibody of the present invention and the fragment thereof are (1) a human anti-human IL-18 antibody for inhibiting human IL-18 from binding to a receptor and (2) a fragment thereof, respectively. Therefore, the antibody and the fragment thereof can be used as therapeutic drugs (treatment method) or preventive drugs (preventive method) for various types of inflammatory disease.

Further, the present invention provides means important in developing IL-18-dependent low-molecular pharmaceutical product (chemosynthetic drug). This is achieved by designing a low-molecular compound in accordance with a higher-order structure of a CDR of an scFv antibody, as will be described later in Examples.

The human anti-IL-18 antibody obtained in the present invention is effective in treating atopic dermatitis, which becomes worse when triggered by infection, and intractable bronchial asthma.

The human anti-IL-18 antibody of the present invention makes it possible to establish a novel method for treating IL-18-dependent inflammation (e.g., natural atopy) not caused by allergen/IgE.

As described above, the human anti-IL-18 antibody of the present invention inhibits IL-18 from binding to a receptor. Therefore, the antibody is effective in treating and preventing the various types of inflammatory disease developed due to IL-18.

In the present invention, an scFv fragment that binds specifically to IL-18 was successfully isolated from a phage display library presenting a human single-chain antibody (scFv fragment). The single-chain antibody can also specifically inhibit IL-18 from binding to a receptor.

The present invention will be described in detail below by way of examples. However, the present invention is not to be limited by these examples and may be varied in many ways within the scope of the present invention.

EXAMPLE 1

(1-1) Construction of a Phage Library from Healthy Persons

Peripheral-blood-derived lymphocytes were taken from twenty healthy persons. A phage library was constructed from the peripheral-blood-derived lymphocytes according to a method reported by J. D. Marks et al. (*J. Mol. Biol.*, 222: 581-597, 1991). $V_{H(\gamma)}$-$V_K$, $V_{H(\gamma)}$-$V_\lambda$, $V_{H(\mu)}$-$V_K$, and $V_{H(\mu)}$-$V_\lambda$ sub-libraries were constructed. It was determined that the $V_{H(\gamma)}$-$V_K$, $V_{H(\gamma)}$-$V_\lambda$, $V_{H(\mu)}$-$V_K$, and $V_{H(\mu)}$-$V_\lambda$ sub-libraries had $1.1 \times 10^8$, $2.1 \times 10^8$, $8.4 \times 10^7$, and $5.3 \times 10^7$ clone diversities, respectively.

(1-2) Panning

Human IL-18 was dissolved in 1 mL of 0.1 M $NaHCO_3$. The resulting solution was allowed to react overnight at 4° C. in a 35 mm dish (manufactured by Iwaki) so as to be immobilized on the dish. Next, the product was subjected to blocking for 2 hours at 20° C. by using 0.5% gelatin/PBS. Thereafter, the product was washed 6 times by using 0.1% Tween20-PBS. To this product, 0.9. ml ($1 \times 10^{12}$ tu/mL) of antibody phage library (single-chain variable region fragment (scFv) derived from healthy persons was added. The mixture was allowed to react.

Next, the reaction liquid was washed 10 times by using 0.1% Tween20-PBS. Thereafter, the reaction liquid was mixed with 1.0 mL of glycine buffer solution, so that an scFv-presenting phage that binds to IL-18 was eluted. The phage thus eluted was mixed with 1 M Tris (hydroxymethyl) aminomethane-HCl, (pH 9.1), so as to adjust a pH of the mixture. Thereafter, the mixture was infected with L-phase *Escherichia coli* TG1. After the infection, TG1 was subjected to centrifugal separation at 3000×g, so as to remove a supernatant. The product was suspended on 200 μL of 2×YT culture medium, inoculated on a SOBAG plate (SOB plate containing 2% glucose and 100 μg/ml of ampicillin), and cultured overnight in an incubator at 30° C. To the colony thus produced in the cultured product, an appropriate amount of 2×YT culture medium was added, so as to suspend and collect the colony with a scraper (Costar).

50 μL of the TG1 liquid was planted in 30 mL of 2×YT culture medium, and then rescued by using a helper phage, so as to prepare a screened phage library. Each of the healthy-person-derived phage libraries $V_{H(\gamma)}$-$V_K$, $V_{H(\gamma)}$-$V_\lambda$, $V_{H(\mu)}$-$V_K$, $V_{H(\mu)}$-$V_\lambda$ was subjected to two steps of panning by using the IL-18-immobilized plate. After the second step of panning, clones were arbitrarily extracted from the SOBAG plate, in order to check for scFv fragment expression and ELISA specificity (screening), and analyze their base sequences.

(1-3) Screening by IL-18 ELISA

ELISA for screening separated clones was carried out by immobilizing human IL-18 on an ELISA plate. Specifically, 2 μg/ml of human IL-18 and 2.5 μg/ml of human serum albumin (HSA) were put in a 40 μL/well ELISA plate (Nunc), allowed to stand for 16 hours at 4° C., and then immobilized on the plate. For blocking, 400 μL/well of PBS solution containing 0.5% BSA, 0.5% gelatin, and 5% skim milk was put in the ELISA plate, and then allowed to stand for 2 hours at 4° C.

Next, into the ELISA plate, 40 μL/well of sample solution containing an scFV-presenting phage was poured, and the mixture was allowed to react. Thereafter, the sample solution was removed, and the product was washed 5 times by using a cleaning liquid. Subsequently, to the immobilized scFv phage, a biotin-labeled anti-M13 monoclonal antibody (Pharmacia biotech) was added, and the mixture was allowed to react with an alkaline phosphatase (AP)-labeled anti-mouse IgG antibody serving as a secondary antibody. The reaction liquid was washed 5 times by using a cleaning liquid. Thereafter, the reaction solution was mixed with 50 μL/well of chromogenic substrate liquid (PBS solution containing 1 g/mL p-nitophenyl phosphate (Wako) and 10% diethanolamine (Wako). The mixture was allowed to exhibit a color for 5 to 10 minutes at room temperature to 37° C. in the shade. The clones were measured for their absorbances at 405 nm by using a Multi-plate Auto Reader NJ-2001 (Inter Med). As a result, it was confirmed that all the clones evaluated were specific to IL-18. The results are shown in FIG. 1.

(1-4) Sequence Analysis of the Clones

Next, respective DNA base sequences of $V_H$ and $V_L$ chains of an scFv gene of the isolated clones were determined by using a Dye terminator cycle sequencing FS Ready Reaction kit (Applied Biosystems). As a result of ELISA and sequence analysis, the isolated clones were categorized into two types (h18-40 and h18-108).

SEQ ID NOS: 1 and 7 represent respective base sequences of $V_H$- and $V_L$-chain genes of clone number h18-108. Further, SEQ ID NOS: 3 and 8 represent respective amino-acid sequences of the $V_H$ and $V_L$ chains.

(1-5) Expression and Purification of Human Anti-IL-18 scFv Fragments

Plasmid DNA was collected from the scFv clones (h18-40 and h18-108) isolated in (1-2, 3) and reacting to human IL-18.

Then, *Escherichia coli* HB1251 was transformed in accordance with an ordinary method. The *Escherichia coli* was cultured overnight in 2×YT culture medium containing 2% glucose and 100 μg/ml of ampicillin, partially transplanted into glucose-free 2×YT culture medium, mixed with IPTG (final concentration of 1 mM) and 100 μg/ml of ampicillin, and further cultured overnight, so as to induce scFv expression. After the incubation, the fungus body was collected by centrifugalization, suspended in PBS containing 1 mM EDTA, and left in ice for 30 minutes. Thereafter, the transformed *Escherichia coli* body was subjected to centrifugal separation at 8900×g for 30 minutes. The supernatant was collected, and then filtered by using a 0.45 μm filter, with the result that a periplasm fraction was obtained. The periplasm fraction served as a starting material from which the scFv fragments were purified.

The material thus prepared was purified in accordance with an ordinary method. The purification was carried out by using affinity chromatography with an anti-E tag antibody. The purified product was dialyzed with PBS. Endotoxin was then removed from the purified product by using an endotoxin-eliminating column Detoxi-gel (PIERCE Inc.) according to the attached protocol. The product was concentrated by using Centricon (Amicon Inc.), which blocks a substance with a molecular weight of 10000 or higher. The product was filtered using a 0.45 μm filter. In this way, a purified sample was obtained.

(1-6) Binding Properties of the Purified scFv Fragments to IL-18

Figure 2:
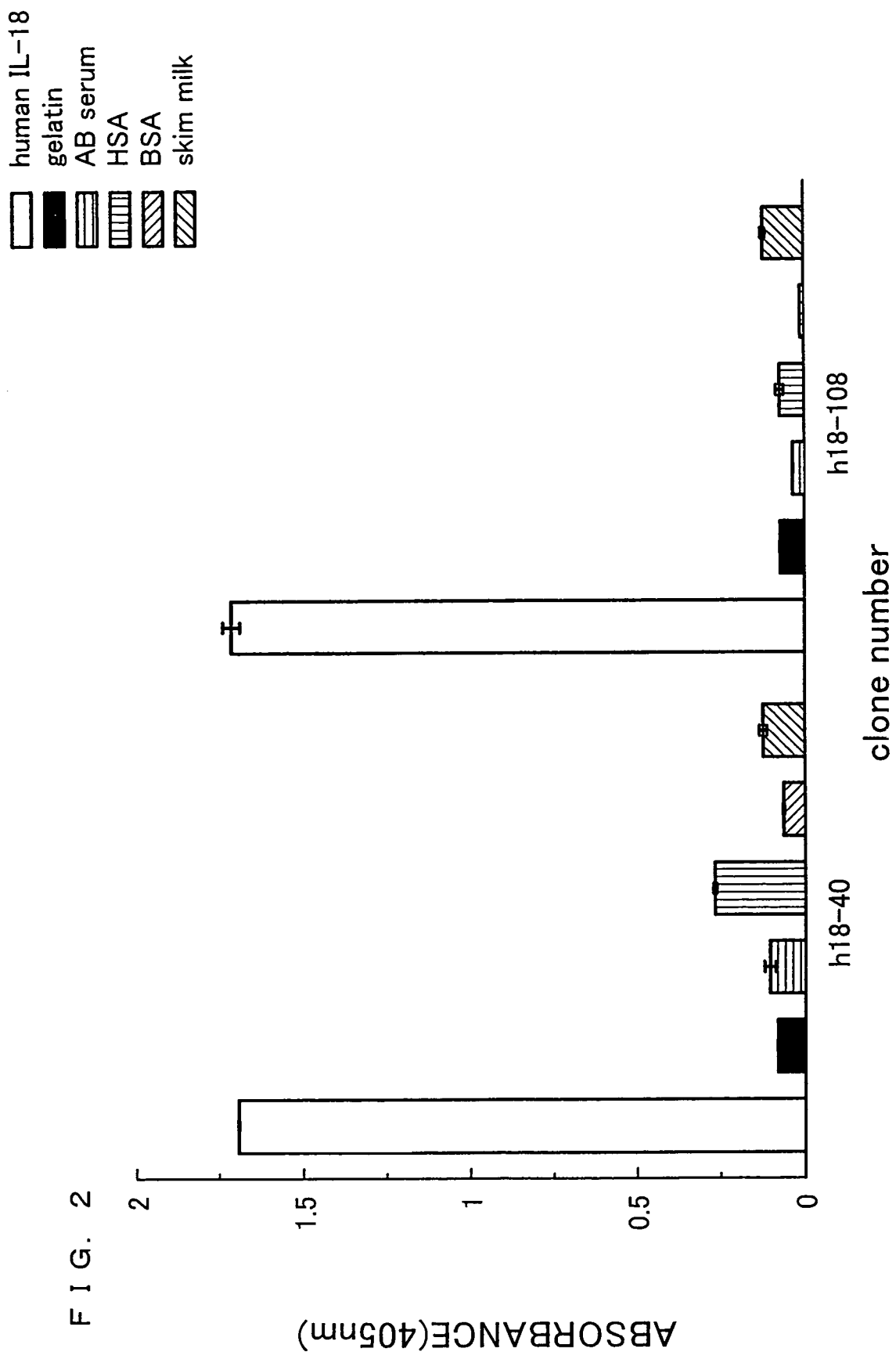
FIG. 2 is a graph showing respective specificities, which are evaluated by ELISA, of human-derived scFv fragments, which are purified in Example 1, with respect to human IL-18.

Next, the purified scFv fragments (h18-40 and h18-108) were measured by ELISA for their binding property to IL-18. A PBS solution of human IL-18 with a concentration of 0.5 μg/mL was immobilized on a 96-well plate (NUNC. MAXISORP). The purified scFv fragment (100 μL) was added to the plate, and then allowed to react for 1 hour at 37° C. The reaction product was washed 5 times with 0.05% Tween-PBS (hereinafter sometimes abbreviated as "PBST"), and then allowed to further react with anti-E tag antibody for 1 hour at 37° C. The reaction product was washed 5 times with PBST. Thereafter, the reaction product was mixed with chromogenic substrate liquid so as to exhibit a color. An absorbance of the product at 405 nm was measured, and a binding property of the product was evaluated. The results are shown in FIG. 2. As shown in FIG. 2, the two types of antibodies (h18-40 and h18-108) were all shown to bind specifically to IL-18.

(1-7) An Effect on IFN-γ Production from Human Marrow Mononuclear KG-1 Cells Stimulated by IL-18.

Figure 3:
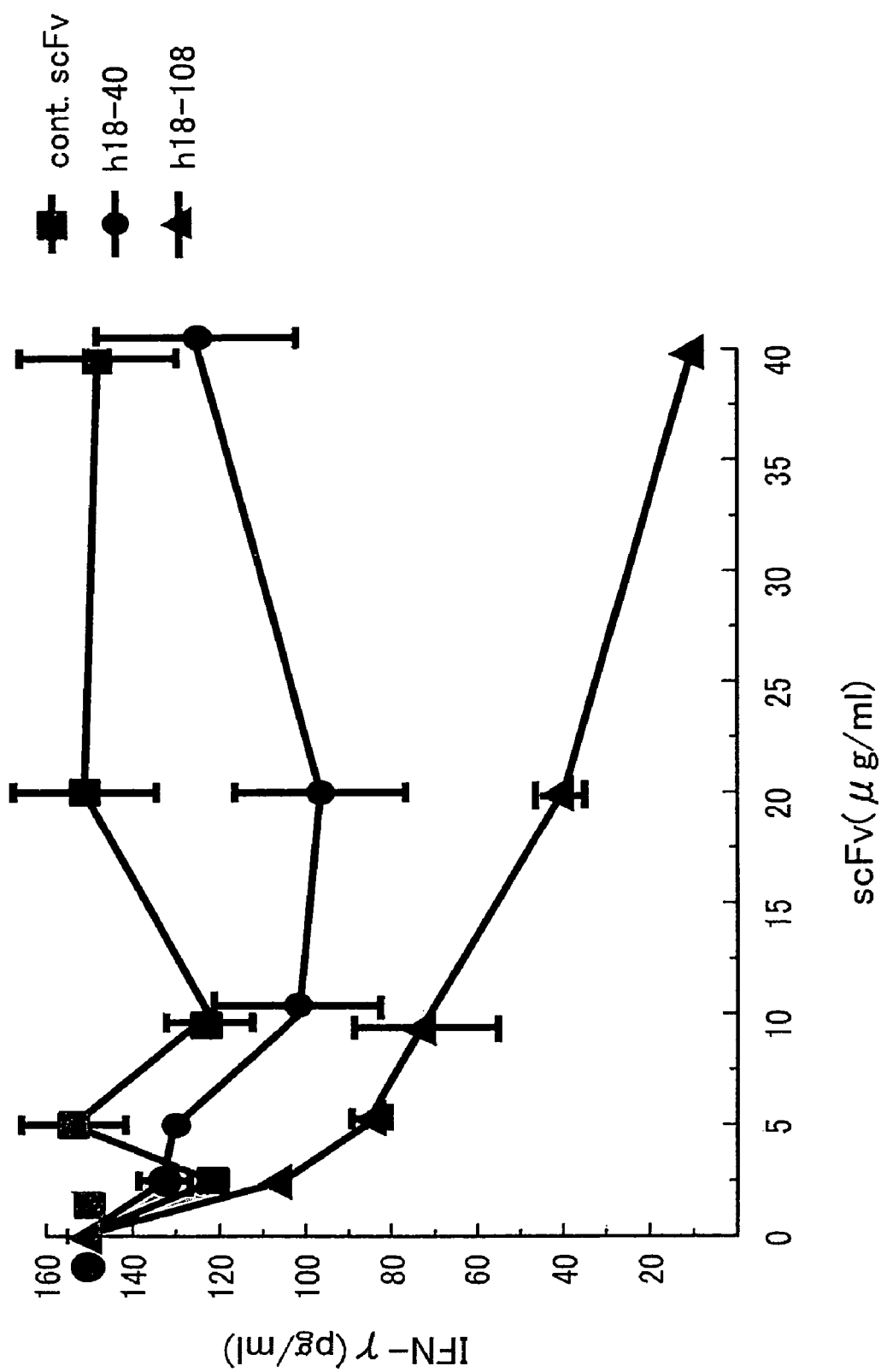
FIG. 3 is a graph indicating that scFv fragments (h18-40 and h18-108) in Example 1 inhibit IL-18 from producing IFN-γ from human marrow mononuclear KG-1 cells.

The scFv fragments were allowed to react with IL-18 (20 ng/100 μL). Thereafter, the reaction product was added to KG-1 cell ($3×10^5$ cells/100 μL) culture solution. After 24 hours of incubation, an amount of INF-γ in the supernatant was measured by ELISA (Biosource). Respective IL-18 inhibitory activities of the scFv fragments (h18-40 and h18-108) were examined based on IFN-γ production from the KG-1 cells. No inhibitory activity was found in the control scFv and the scFv (h18-40). The scFv (h18-108) concentration-dependently inhibited the KG-1 cells from producing INF-γ. The results are shown in FIG. 3.

(1-8) A Binding Inhibition Effect of IL-18 on Human Marrow Mononuclear KG-1 Cells Biotin-labeled IL18 (400 ng/50 μL) and the scFv fragment (control scFv or h18-108) were allowed to react with each other. Thereafter, the reaction product was added to KG-1 cell ($1×10^6$ cells/50 μL) culture solution, allowed to react with phycoerythrin-labeled streptoavidin (Betcon Dickinson), and subjected to flow cytometry analysis (Beckman Coulter).

Figure 4:
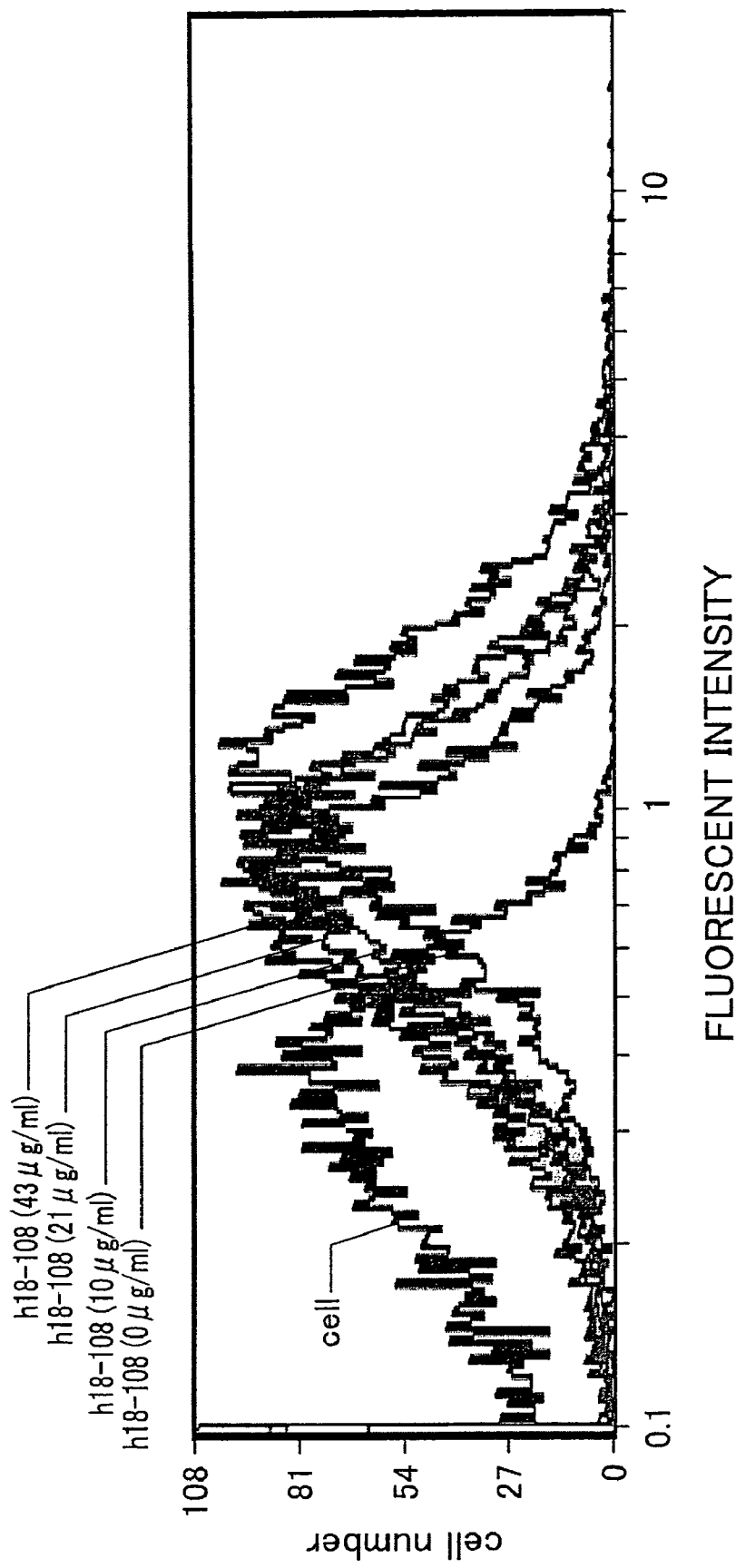
FIG. 4 is a graph indicating that the scFv fragment (h18-108] in Example 1 inhibits IL-18 from binding to the human marrow mononuclear KG-1 cells.
Figure 5:
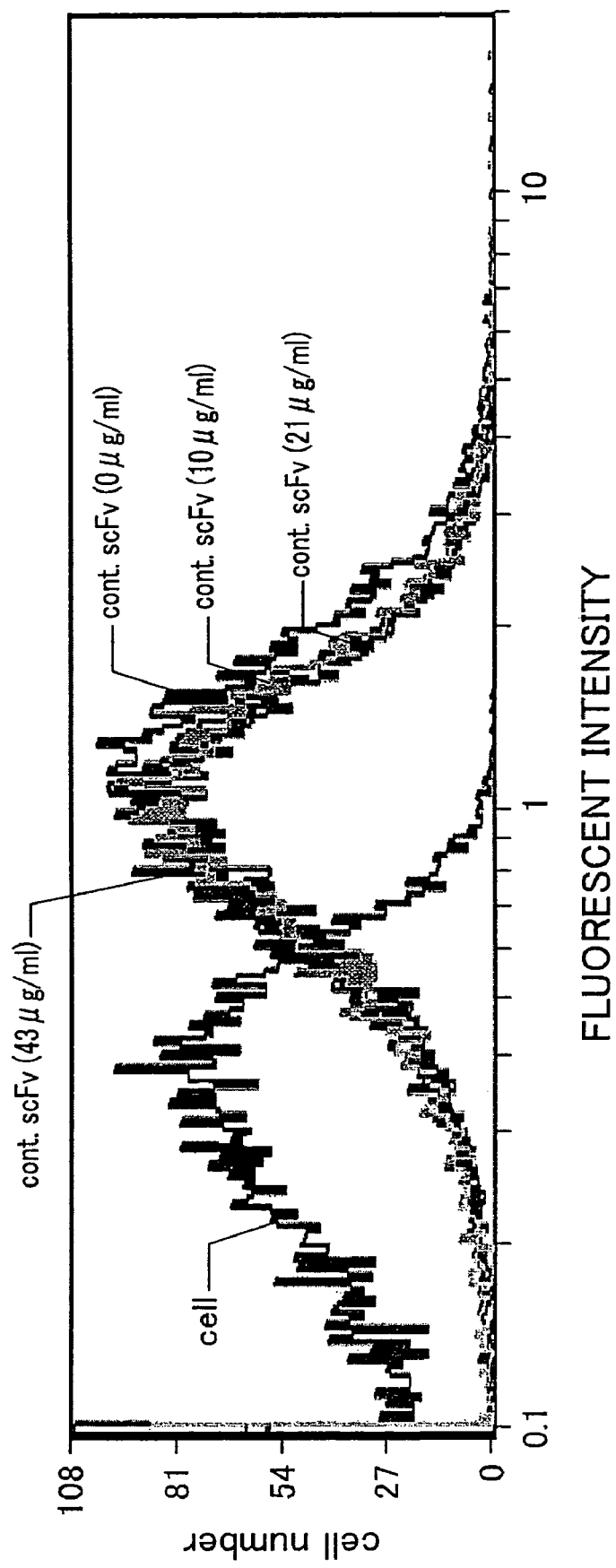
FIG. 5 is a graph showing results obtained from control scFv in FIG. 4.

As shown in FIGS. 4 and 5, the flow cytometry analysis was conducted to examine whether the scFv fragment (h18-108) inhibits IL-18 from binding to the KG-1 cells. As a result, no change was found in the way the control scFv fragment inhibited IL-18 from binding to the KG-1 cells (FIG. 4). In contrast, the scFv fragment (h18-108) concentration-dependently inhibited IL-18 from biding to the KG-1 cells (FIG. 5).

(1-9) A Property of the scFV Fragment (h18-108)

Figure 6:
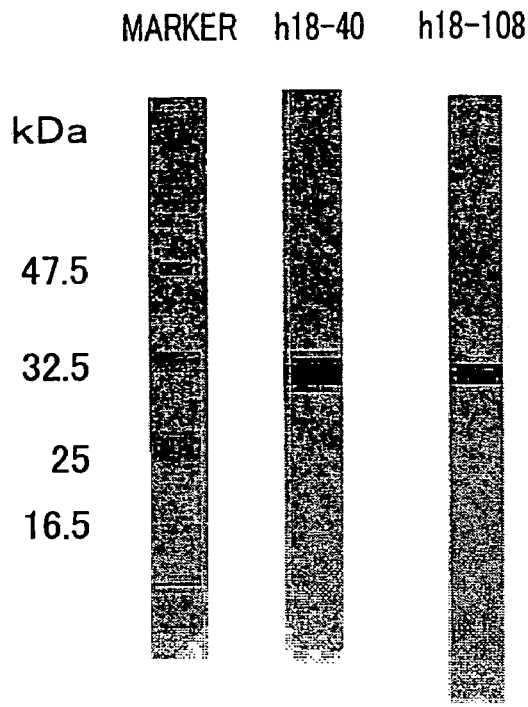
FIG. 6 is a diagram showing results obtained through western blotting of the scFv fragment (h18-108).
Figure 7:
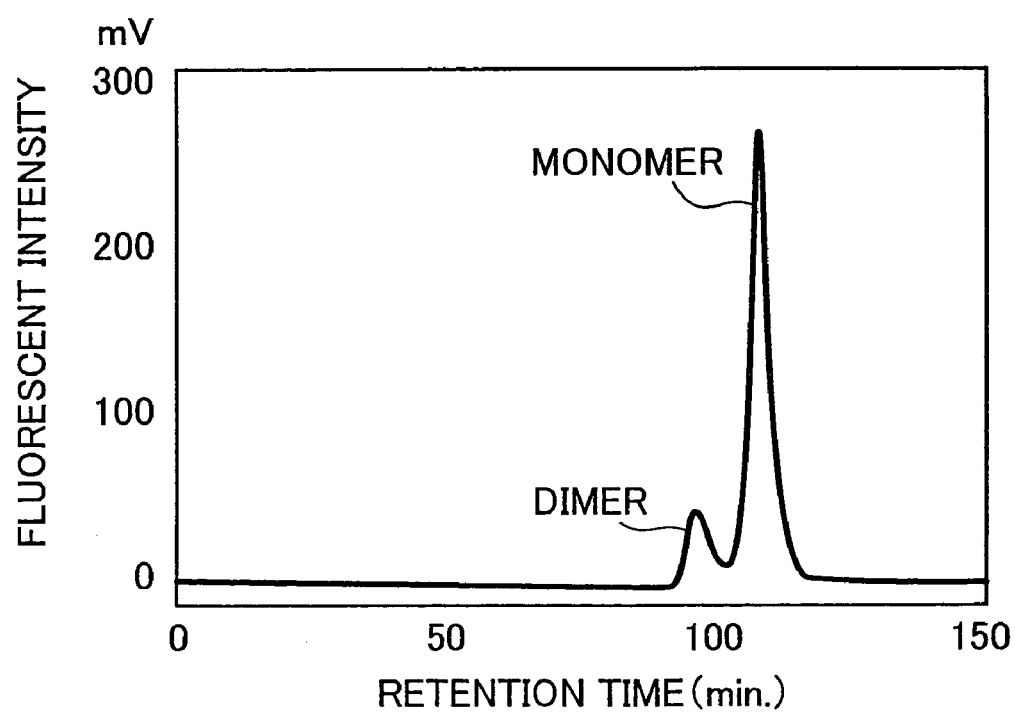
FIG. 7 is a graph showing results obtained through gel filtration chromatography of the scFv fragment (h18-108).

The scFv fragment (h18-108), which exhibits specificity to human IL-18, was subjected to western blotting. As a result, as shown in FIG. 6, a molecular weight of the scFv fragment (h18-108) was approximately 30 kDa. Further, the scFv fragment (h18-108) was subjected to gel filtration chromatography. As a result, as shown in FIG. 7, the separation pattern showed that 90% of the scFv fragments expressed by the clone (h18-108) were monomers, and the remaining 10% were dimers.

EXAMPLE 2

In Example 2, cytokines produced from IL-18-stimulated Th1 and Th2 cells were studied.

(2-1) Reagents

Recombinant human IL-2, IL-4, IL-12, and INF-γ were purchased from R&D (Minneapolis, Mnn.). Recombinant human IL-18 was purchased from MBL Inc. (Nagoya, Japan). FITC (fluorescein isothiocyanate)- or Cychrome (cytochrome)-anti-human CD4 mAb (monoclonal antibodies), FITC-anti-human CD45RA mAb, FITC-anti-human IFN-γ mAb, PE-anti-human IL-13 mAb, and anti-human IL-12 mAb were purchased from Pharmingen (San Diego, Calif.). PE-anti-human IL-18Rα mAb (Clone 70625), anti-human CD3ε mAb, and anti-human IL-14 mAb were purchased from R&D.

(2-2) Production of Th1 or Th2 Cells in Vitro

Naive $CD4^+CD45RA^+T$ cells were isolated from peripheral blood of healthy donors (K. Nakanishi et al., *Int. Immunol.* 12:151.). Th1 and Th2 cells were produced by culturing, in a 24-well plate, $CD4^+CD45RA^+T$ cells ($1×10^6$/mL) with either (i) PHA (1 μg/mL), IL-12 (50 μg/mL), and neutralizing anti-IL-4 mAb (500 ng/mL), or (ii) PHA (1 μg/mL), IL-4 (200 μg/mL), and neutralizing anti-IL-12 mAb (10 μg/mL). These stimulated T cells were washed after 3 days and cultured for additional 4 days in a culture medium containing 100 U/mL of IL-12.

(2-3) Isolation of INF-$\gamma^+$ Th1 Cells For isolation of INF-$\gamma^+$ Th1 cells, polarized Th1 cells were cultured with immobilized anti-CD3 (5 μg/mL) and IL-2 (100 U/mL) in a 24-well plate. Next, the cultured product was subjected to treatment to enrich IFN-γ-expressing living Th1 cells. After 3 hours, only adherent cells were collected and incubated for 5 minutes on ice with an anti-CD45/anti-INF-γ bispecific antibody (Miltenyi Biotec). The treated cells were transferred to 50 ml conical tubes and cultured at a concentration of $5×10^4$ cells/ml in 20 ml of a warmed medium and placed in a 37° C. water bath. After 30 minutes, the cells were washed with a cold phosphate buffer solution (PBS) containing 0.5% bovine serum albumin (BSA). Matrix-captured IFN-γ was detected by using PE-anti-human IFN-γ, and was securely isolated with anti-PE microbeads by using auto MACS.

(2-4) In Vitro Culture

Newly polarized Th1 and Th2 cells, as well as INF-$\gamma^+$ cells sorted from newly polarized Th1 cells, were recultured in $1×10^5$/0.2 mL well containing immobilized anti-CD3 (5 μg/mL). This was performed in the presence of various concentrations of IL-18. After 6 to 72 hours of incubation, supernatants were collected and measured by ELISA (R&D) for IL-4, IL-5, IL-8, IL-13, IFN-γ, and GM-CSF contents.

(2-5) Flow Cytometry

Polarized. Th1 cells ($1\times10^6$/mL) were restimulated for 72 hours by immobilized anti-CD3 with or without IL-18 (100 ng/mL) in a 24-well plate. During the last 3 hours, 2 μM monensin was added to inhibit cytokine secretion. The analysis of intracellular INF-γ$^+$ and/or IL-13$^+$ staining was conducted according to a document (K. Nakanishi et al., *J. EXP. Med.*, 2004, 199, 535-545). A level of IL-18Ra expression on Th1 and Th2 cells was measured in the following manner. FcR was blocked by human IgG. Then, the cells were incubated with either (i) FITC-anti-human CD4 and PE-anti-human IL-18Rα chain mAb, or (ii) control PE-mouse IgG1 mAb for 30 minutes at 4° C. in PBS containing 1% FCS. The samples thus obtained were analyzed on a FACS Calibur (BD Bioscience, San Jose, Calif.).

(2-6) Experimental Results

According to (2-2) to (2-5), naive CD4$^+$CD45RA$^+$T cells isolated from peripheral blood of healthy donors were stimulated in vitro under Th1 and Th2 cell inducing conditions for 7 consecutive days.

Figure 8:
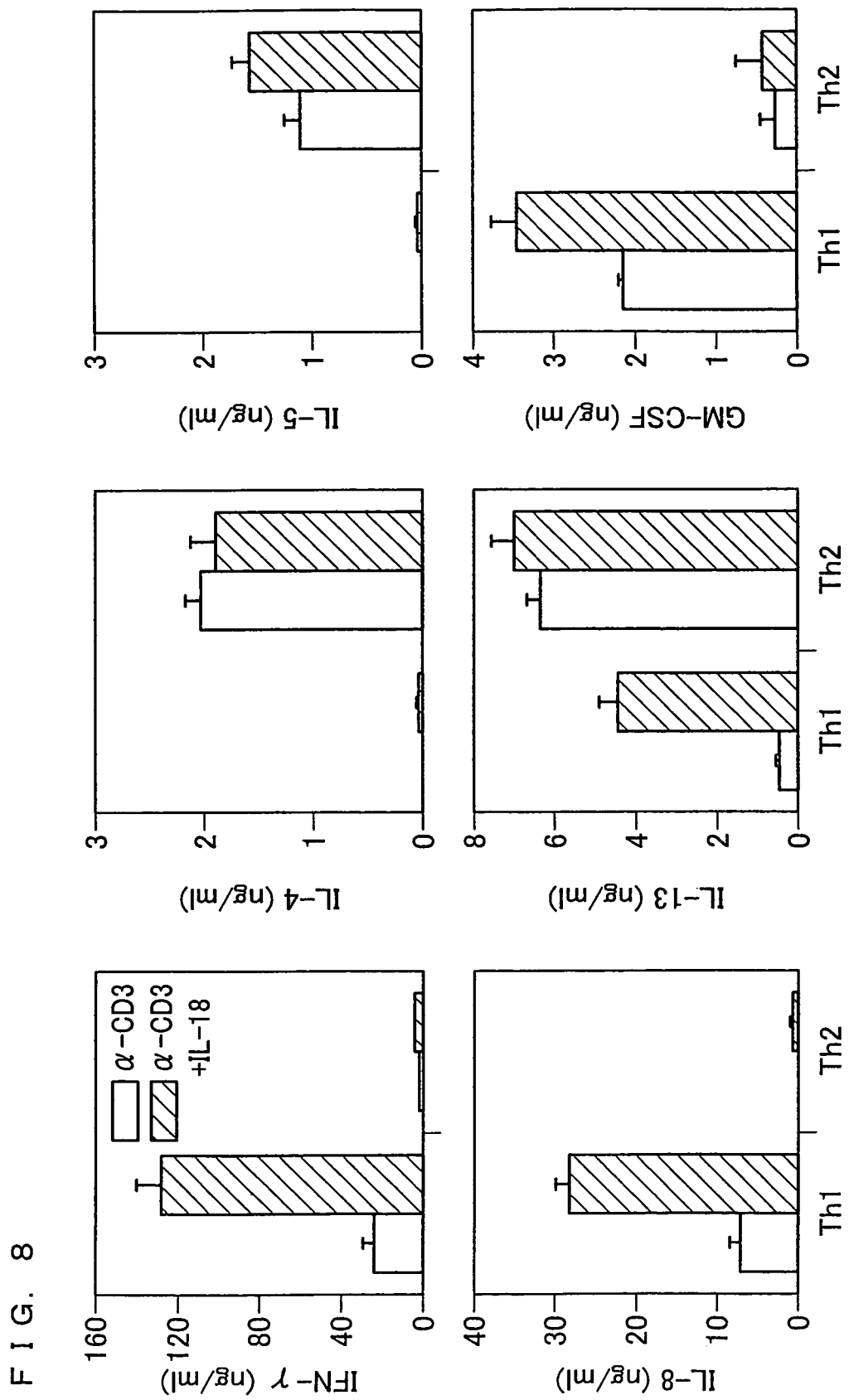
FIG. 8 is a graph showing respective amounts of cytokines produced from Th1 and Th2 cells stimulated in Example 2.

The results are shown in FIG. 8. FIG. 8 shows results (α-CD3) obtained by stimulating the naive CD4$^+$CD45RA$^+$T cells with immobilized anti-CD3 alone, and results (α-CD3+ IL-18) obtained by stimulating the naive CD4$^+$CD45RA$^+$T cells with immobilized anti-CD3 and IL-18.

As shown in FIG. 8, when the Th2 cells were stimulated with immobilized anti-CD3, the Th2 cells produced large amounts of IL-4, IL-5, and IL-13 but did not produce IFN-γ. Further, the Th1 cells mainly produced IFN-γ, IL-18, and GM-CSF.

Further, as shown in FIG. 8, stimulation with immobilized anti-CD3 plus IL-18 failed to enhance Th2 cytokine production from the Th2 cells. In contrast, the treatment remarkably enhanced production of IFN-γ, IL-8, IL-13, and GM-CSF from the Th1 cells.

Figure 9:
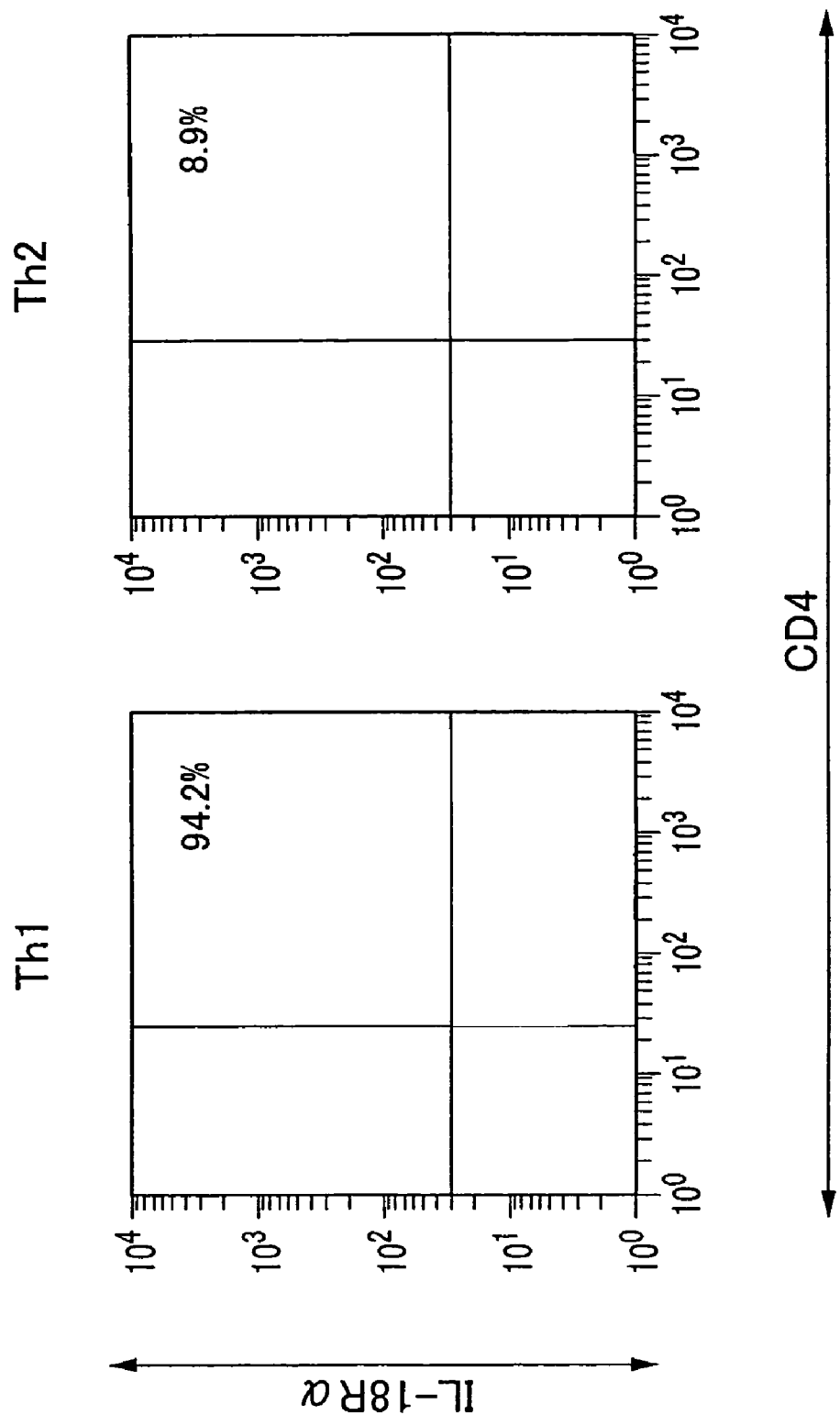
FIG. 9 is a graph showing levels of IL-18Rα chain expression on respective surfaces of the Th1 and Th2 cells stimulated in Example 2.

The mechanism underlying this difference in IL-18 responsiveness between the Th1 and Th2 cells can be principally explained by preferential expression of IL-18Rα chains on the Th1 cells. FIG. 9 is a diagram showing expression levels of IL-18Rα chains on the surface of the Th1 and Th2 cells by the foregoing stimulation. As shown in FIG. 9, human Th1 cells express a high level of IL-18Rα chains, while human Th2 cells express a meager level of IL-18Rα chains. Thus, IL-18 Rα expressing human Th1 cells has the property of producing Th1 cytokines, Th2 cytokines, and GM-CSF in response to anti-CD3 plus IL-18.

Figure 10:
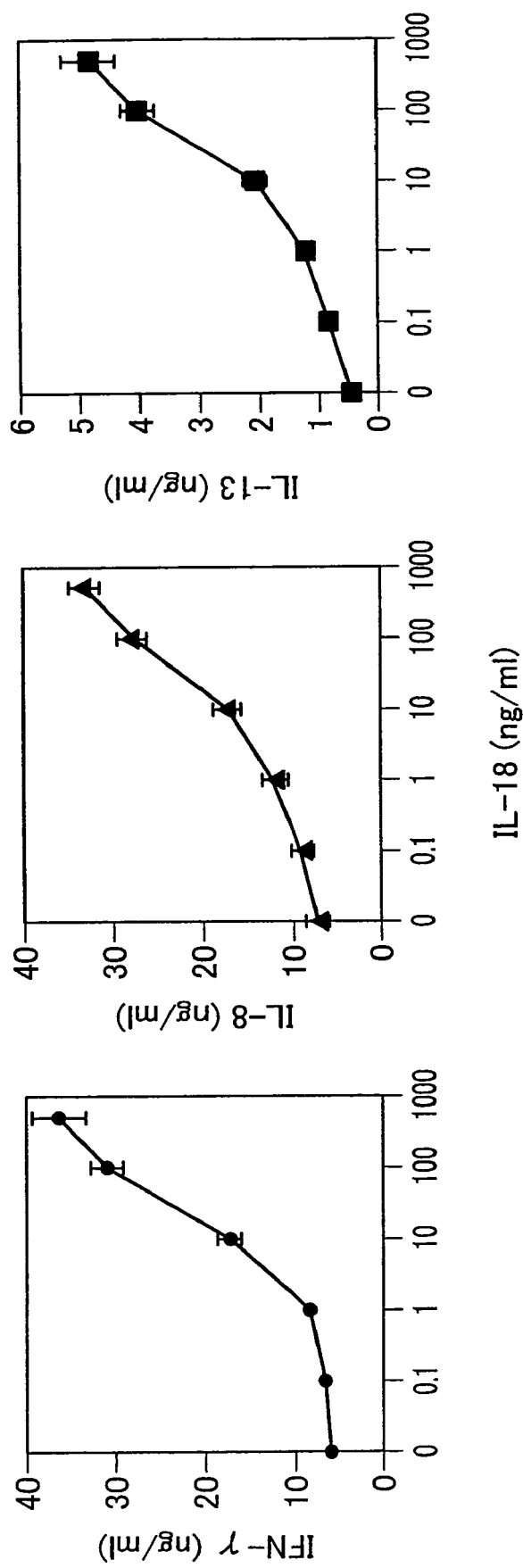
FIG. 10 is a graph showing respective amounts of cytokines produced from Th1 cells in response to various doses of IL-18 in Example 2.

Meanwhile, IL-18-dose responsiveness of anti-CD3-stimulated Th1 cells (in terms of IFN-γ, IL-8, and IL-13 production) was examined. Accordingly, the Th1 cells were stimulated for 3 days with various doses of IL-18 (up to 500 ng/mL) in the presence of immobilized anti-CD3. FIG. 10 is a graph showing respective amounts of cytokines produced from the Th1 cells in response to various doses of IL-18. As shown in FIG. 10, the Th1 cells does-dependently increased IFN-γ, IL-8, and IL-13 production in the presence of IL-18. Further stimulation of the anti-CD3-stimulated Th2 cells with IL-18 failed to enhance their cytokine production responses. Therefore, as shown in FIG. 10, only the human Th1 cells exhibit a unique effect of producing GM-CSF and IL-8, as well as Th1 and Th2 cytokines, in response to an antigen plus IL-18.

Thus, IL-18 induced the polarized human Th1 cells to produce IFN-γ, IL-8, and IL-13.

Next, kinetic characteristics of the cytokines produced after stimulation with anti-CD3 and IL-18 were examined.

Figure 11:
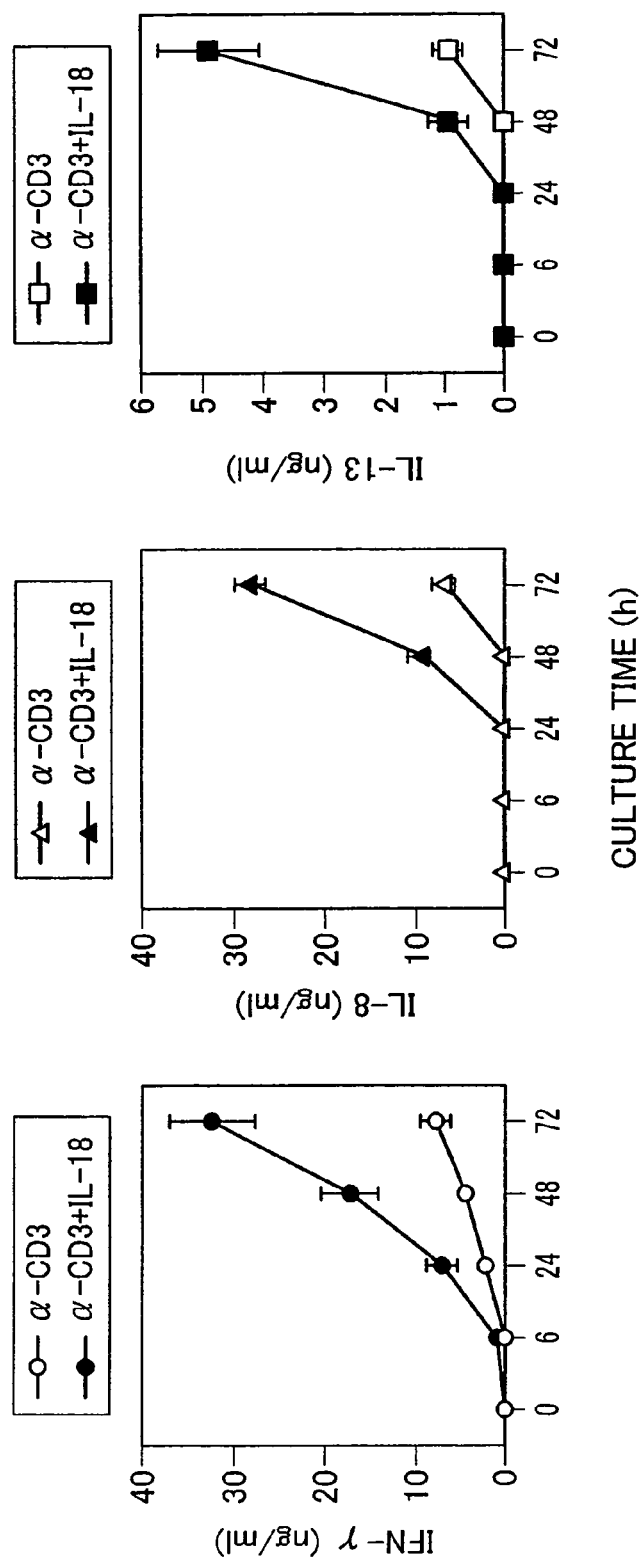
FIG. 11 is a graph showing relationships between respective amounts of cytokines produced from the Th1 cells and durations of culture after stimulation of the Th1 cells in Example 2.

FIG. 11 is a graph showing relationships between respective amounts of cytokines produced from the Th1 cells and durations of culture after stimulation of the Th1 cells. As shown in FIG. 11, the Th1 started to produce IFN-γ at a relatively early stage of stimulation. Even after 24 hours of stimulation with anti-CD3, a large amount of IFN-γ was detected. In contrast, neither IL-8 nor IL-13 was detected at this point of time. However, after 72 hours of stimulation, both IL-8 and IL-13 were detected. Therefore, it was originally assumed that the Th1 cells produce only IFN-γ, because Th1 cells are usually stimulated for only 48 hours for measurement purposes. However, as shown in FIG. 11, IL-8 and IL-13 were detected after 72 hours of stimulation. Most importantly, additional IL-18 stimulation caused the anti-CD3-stimulated Th1 cells to produce the cytokines more quickly and in larger quantity. Thus, IL-18 stimulation accelerated and increased production of IFN-γ, IL-8, and IL-13 from the Th1 cells.

As described above, IL-18 stimulation dose-dependently induces the anti-CD3-stimulated Th1 cells to produce IFN-γ, IL-8, and IL-13 (FIG. 10). However, it is still necessary to eliminate the possibility of Th0 cells producing IFN-γ and IL-13 in response to an antigen and IL-18. In order to eliminate this possibility, the proportions of CD4$^+$ T cells positive - for cytoplasmic INF-γ and/or IL-13 in IL-18-stimulated Th1 cells were examined by FACS analysis. The results are shown in FIG. 12.

Figure 12:
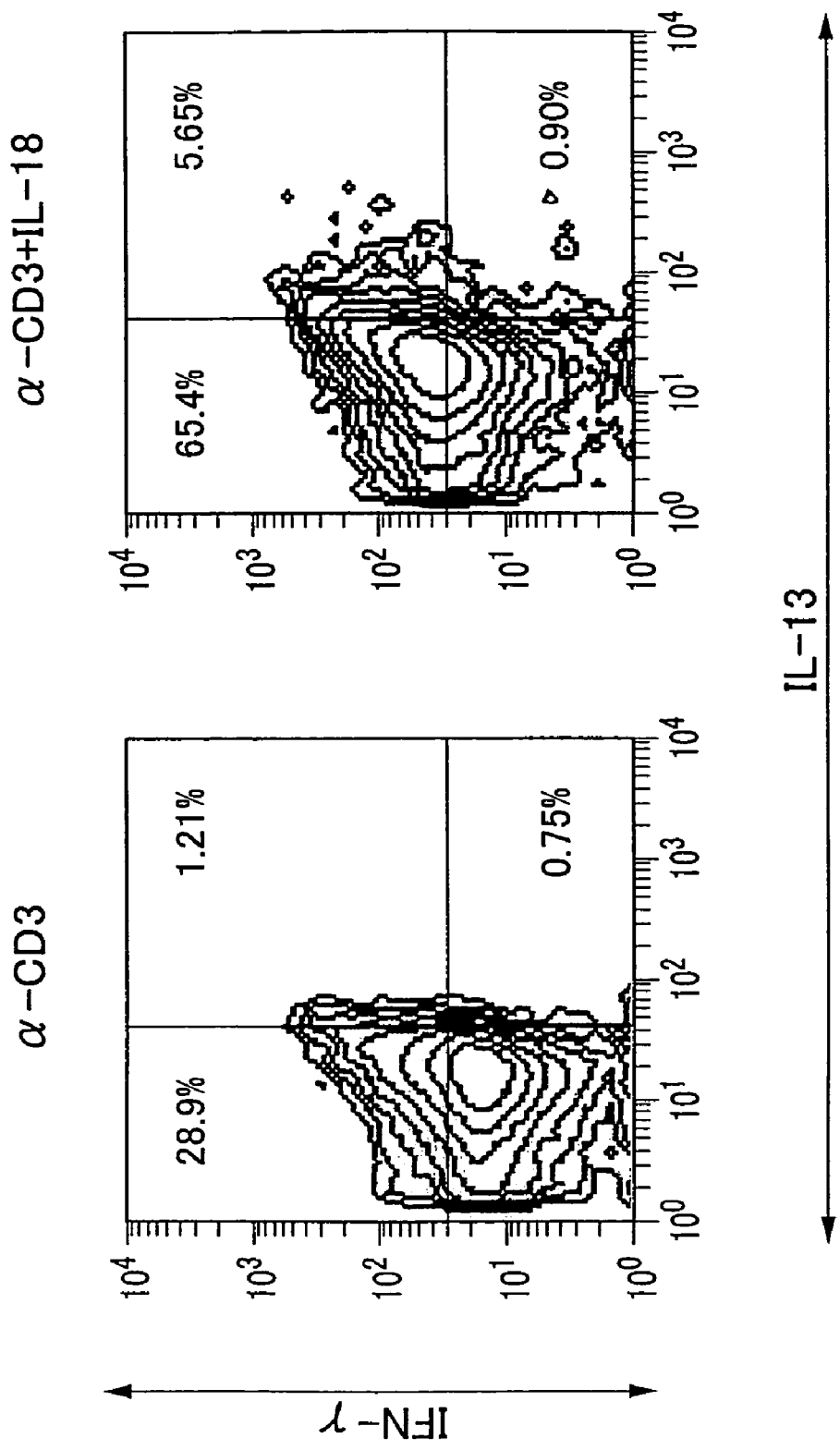
FIG. 12 is a diagram showing results obtained through FACS analysis of a proportion of $CD4^+$ T cells positive for cytoplasmic INF-γ and/or IL-13 in IL-18-stimulated Th1 cells in Example 2.

As shown in FIG. 12, 5.65% of the human Th1 cells stimulated with immobilized CD-3 plus IL-18 were positive for cytoplasmic INF-γ and IL-13, whereas only 1.21% of the Th1 cells treated with anti-CD3 alone were positive for cytoplasmic INF-γ and IL-13. The specificity of intercellular INF-γ or IL-13 staining is indicated by the fact that isotype-matched control antibodies are not stained. Furthermore, such staining is completely blocked by pretreatment with excessive recombinant human IFN-γ or IL-13 (data not shown). These results indicate that the Th1 cells produce IFN-γ or IL-13 when stimulated with anti-CD3 plus IL-18.

Next, induction of IL-13 production from IFN-γ$^+$ Th1 cells by IL-18 was examined. It is important to examine the possibility that the. Th1 cells, which produce INF-γ, also produce IL-13 when stimulated with anti-CD3 and IL-18. Accordingly, INF-γ-expressing Th1 cells were purified by capturing secreted INF-γ by surface-bound anti-INF-γ antibodies.

Figure 13:
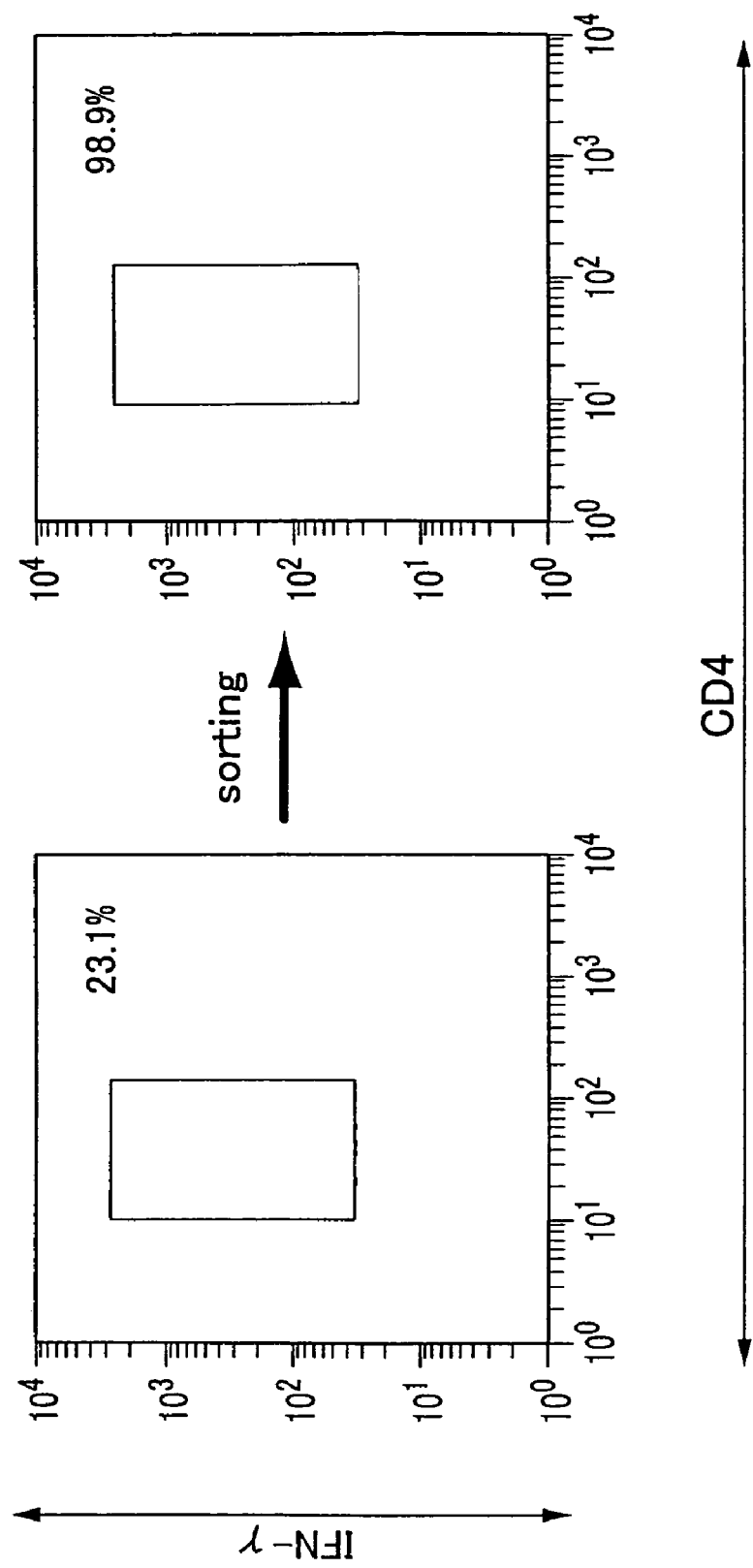
FIG. 13 is a diagram showing a proportion of IFN-$γ^+$ Th1 cells in anti-CD3-stimulated Th1 cells and an example of sorting positive IFN-$γ^+$ Th1 cells in Example 2.
Figure 14:
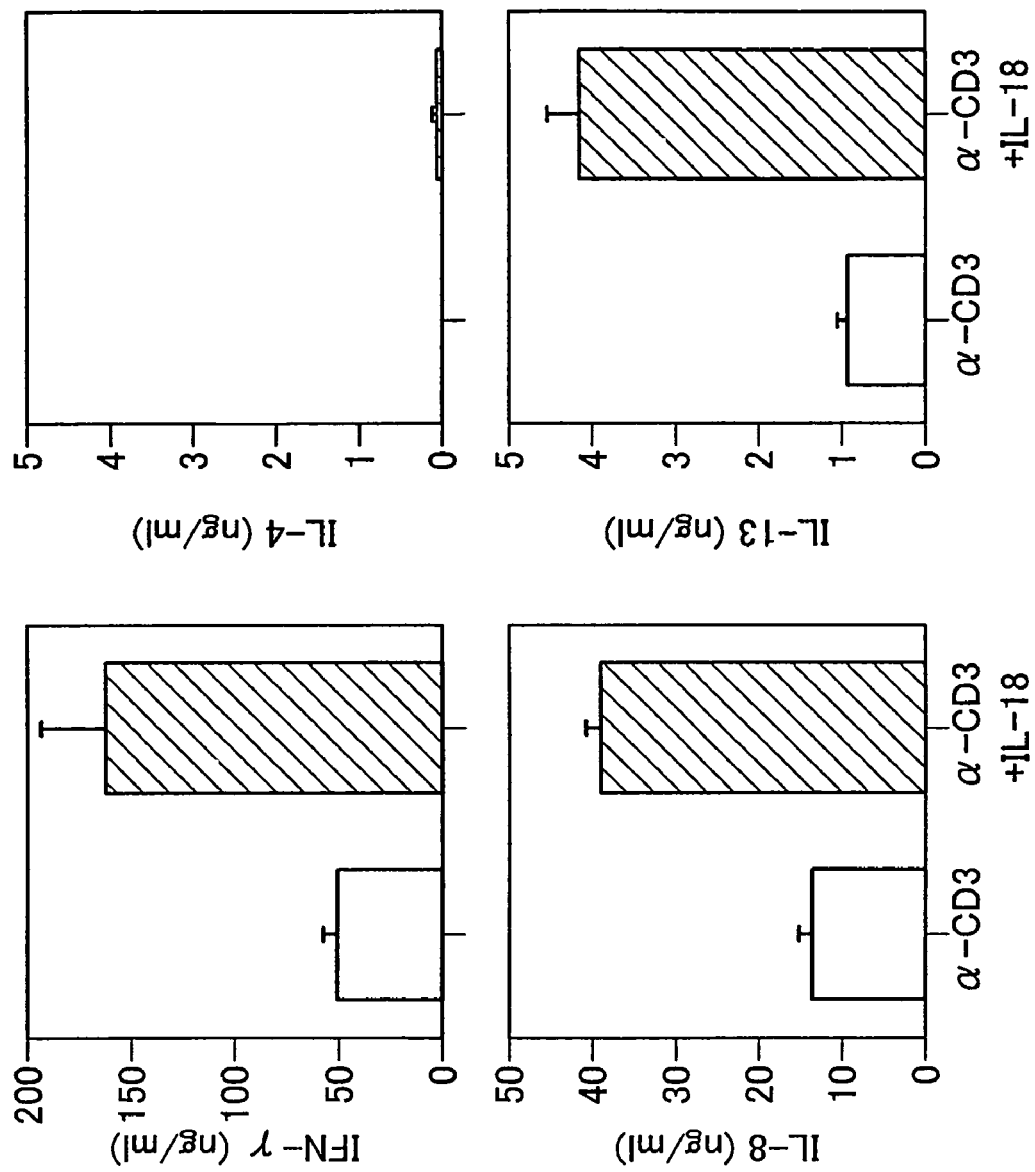
FIG. 14 is a graph showing respective amounts of cytokines produced from IFN-$γ^+$ Th1 cells stimulated with anti-CD3 plus IL-18 in Example 2.

FIG. 13 is a diagram showing a proportion of IFN-γ$^+$ Th1 cells in anti-CD-stimulated Th1 cells and an example of sorting positive IFN-γ$^+$ Th1 cells. As shown in FIG. 13, 23.1% of the Th1 cells stimulated with anti-CD3 expressed IFN-γ on their surfaces. Then, those Th1 cells (IFN-γ$^+$ Th1 cells) which expressed IFN-γ on their surfaces were sorted as positive by using auto MACS, so that IFN-γ$^+$CD4$^+$ Th1 cells were purified with a degree of purity of 99%. The IFN-γ$^+$ Th1 cells thus obtained were cultured with anti-CD3 and IL-18 so as to be stimulated. FIG. 14 is a graph showing respective amounts of cytokines produced from the IFN-γ$^+$ Th1 cells due to the stimulation. As shown in FIG. 14, the stimulation greatly increased IFN-γ, IL-8, and IL-13 production but did not increase IL-4 production. Therefore, it can be concluded that highly purified IFN-γ-expressing living human Th1 cells strongly express IL-18Rα chains on their surfaces and, when stimulated with anti-CD3 and IL-18, produce IFN-γ, IL-8, and IL-13. These results indicate that when human Th1 cells whose TCRs (T cell receptors) have antigens binding thereto are further stimulated with IL-18, the human Th1 cells increase IFN-γ, IL-8, and IL-13 production. Note that FIGS. 8, 10, 11, 13, and 14 show respective representative values of four independent experiments, and the same results were obtained in the experiments.

As described above, when Th1 cells are stimulated with an antigen plus IL-18, the Th1 cells produce Th1 cytokines (INF-γ, etc.), Th2 cytokines (IL-9, IL-13, etc.), chemokines (RANTES, MIP-1α, etc.), and GM-CSF. Stimulation of a tract epithelium with INF-γ and IL-13 causes the most severe bronchial asthma. Therefore, by inhibiting the activity of IL-13 through administration of the scFv fragment of Example 1, it becomes possible to treat severe bronchial asthma.

The embodiments and concrete examples of implementation discussed in the foregoing detailed explanation serve solely to illustrate the technical details of the present invention, which should not be narrowly interpreted within the limits of such embodiments and concrete examples, but rather may be applied in many variations within the spirit of the present invention, provided such variations do not exceed the scope of the patent claims set forth below.

INDUSTRIAL APPLICABILITY

As described above, an anti-human IL-18 antibody of the present invention and a fragment thereof are of human origin. This makes it possible to provide a therapeutic drug that exhibits a remarkable therapeutic effect and a high level of safety even when administered repeatedly or for a prolonged time period in treatment of disease caused directly or indirectly by IL-18.

The invention claimed is:

1. An isolated human antibody, comprising
   human immunoglobulin VH-chain CDR1, CDR2, and CDR3 of a polypeptide consisting of amino-acid sequences represented by SEQ ID NOS: 4, 5, and 6, respectively; and
   human immunoglobulin VL-chain CDR1, CDR2, and CDR3 of a polypeptide consisting of amino-acid sequences represented by SEQ ID NOS: 10, 11, and 12, respectively.

2. An isolated human antibody, comprising:
   a polypeptide consisting of the amino-acid sequence represented by SEQ ID NO: 3; and
   a polypeptide consisting of the amino-acid sequence represented by SEQ ID NO: 9.

3. An isolated human antibody, comprising:
   ligation of a polypeptide consisting of the amino-acid sequence represented by SEQ ID NO: 3 and
   a polypeptide consisting of the amino-acid sequence represented by SEQ ID NO: 9.

4. A detector for human interleukin-18, the detector comprising the antibody according to any one of claims 1-3.

5. An immunological disease diagnostic kit for measuring an amount of human interleukin-18 contained in a test sample comprising the human interleukin-18 antibody according to any one of claims 1-3; and a carrier on which the human interleukin 18 antibody is immobilized.

6. A human interleukin-18 activity inhibitor comprising a human interleukin-18 antagonist as an active ingredient, the human interleukin-18 antagonist being the human antibody according to any one of claims 1-3.

7. The human interleukin-18 activity inhibitor according to claim 6, which is used for treating an immunological disease associated with increased IL-18.

8. The human interleukin-18 activity inhibitor according to claim 7, which inhibits cytokine production from helper T1 cells stimulated with an antigen and human interleukin-18.

9. The human interleukin-18 activity inhibitor according to claim 7, wherein the immunological disease is allergy or inflammation.

10. An isolated cDNA encoding a human antibody comprising:
    human immunoglobulin VH-chain CDR1, CDR2, and CDR3 of a polypeptide consisting of amino-acid sequences represented by SEQ ID NOS: 4, 5, and 6, respectively; and
    human immunoglobulin VL.-chain CDR1, CDR2, and CDR3 of a peptide consisting of amino-acid sequences represented by SEQ ID NOS: 10, 11, and 12, respectively.

11. The cDNA according to claim 10, including as an open reading frame the nucleic acid sequence of SEQ ID NO: 1 and 7.

12. A recombinant expression vector, comprising the cDNA according to claim 11.

13. A transformant, comprising the cDNA according to claim 11 introduced therein.

14. A method for producing a human antibody against human interleukin-18, comprising the steps of:
    introducing the cDNA according to claim 11 into a host; and
    causing the host to express the cDNA thus expressed.

15. A recombinant expression vector, comprising the cDNA according to claim 10.

16. An isolated transformant, comprising the cDNA according to claim 10 introduced therein.

17. A method for producing a human antibody against human interleukin-18 by causing a host to express the cDNA according to claim 10.

18. The isolated cDNA according to claim 10, wherein the cDNA encodes a human anti-human interleukin-18 antibody having (1) binding activity to human interleukin-18 and (2) inhibitory activity for human interleukin-18.

19. An isolated cDNA encoding a human antibody, wherein the cDNA encodes:
 a polypeptide consisting of the amino-acid sequence represented by SEQ ID NO: 3; and
 a polypeptide consisting of the amino-acid sequence represented by SEQ ID NO: 9.

20. (cDNA) An isolated cDNA encoding a human antibody, wherein the cDNA encodes:
 ligation of a polypeptide consisting of the amino-acid sequence represented by SEQ ID NO: 3 a polypeptide consisting of the amino-acid sequence represented by SEQ ID NO: 9.

21. A method for diagnosing an immunological disease associated with increased IL-18 comprising: measuring the amount of human interleukin-18 contained in a test sample by using a human antibody comprising:
 human immunoglobulin VH-chain CDR1, CDR2, and CDR3 of a polypeptide consisting of amino-acid sequences represented by SEQ ID NOS: 4, 5, and 6, respectively; and
 human immunoglobulin VL-chain CDR1, CDR2, and CDR3 of a peptide consisting of amino-acid sequences represented by SEQ ID NOS: 10, 11, and 12, respectively.

22. The method according to claim 21, wherein the antibody is a human anti-human interleukin-18 antibody having (1) binding activity to human interleukin-18 and (2) inhibitory activity for human interleukin-18.

23. The method of claim 22, wherein the immunological disease is atopic dermatitis, airway inflammation, airway hyperresponsiveness (AUR), or asthma.

24. The method of claim 21, wherein the immunological disease is atopic dermatitis, airway inflammation, airway hyperresponsiveness (AER), or asthma.

25. A method for diagnosing an immunological disease associated with increased IL-18, comprising measuring the amount of human interleukin-18 contained in a test sample by using a human antibody comprising:
 a polypeptide consisting of the amino-acid sequence represented by SEQ ID NO: 3; and
 a polypeptide consisting of the amino-acid sequence represented by SEQ ID NO: 9.

26. The method of claim 25, wherein the immunological disease is atopic dermatitis, airway inflammation, airway hyperresponsiveness (AHR), or asthma.

27. A method for diagnosing an immunological disease associated with increased IL-18, comprising measuring the amount of human interleukin-18 contained in a test sample by using a human antibody comprising: a ligation of a polypeptide consisting of the amino-acid sequence represented by SEQ ID NO: 3 and a polypeptide consisting of the amino-acid sequence represented by SEQ ID NO: 9.

28. The method of claim 27, wherein the immunological disease is atopic dermatitis, airway inflammation, airway hyperresponsiveness (AHR), or asthma.

* * * * *